US011248200B2

(12) United States Patent
Ni et al.

(10) Patent No.: US 11,248,200 B2
(45) Date of Patent: Feb. 15, 2022

(54) CELL CULTURE DEVICE AND CELL CULTURE SYSTEM

(71) Applicant: NATIONAL TSING HUA UNIVERSITY, Hsinchu (TW)

(72) Inventors: Bing-Syuan Ni, Hsinchu (TW); Jen-Huang Huang, Hsinchu (TW)

(*) Notice: Subject to any disclaimer, the term of this patent is extended or adjusted under 35 U.S.C. 154(b) by 531 days.

(21) Appl. No.: 16/194,025

(22) Filed: Nov. 16, 2018

(65) Prior Publication Data
US 2020/0123490 A1 Apr. 23, 2020

(30) Foreign Application Priority Data
Oct. 22, 2018 (TW) .................................. 107137237

(51) Int. Cl.
*C12M 3/00* (2006.01)
*C12M 1/00* (2006.01)
*C12M 1/34* (2006.01)

(52) U.S. Cl.
CPC ............ *C12M 23/42* (2013.01); *C12M 23/22* (2013.01); *C12M 23/34* (2013.01); *C12M 23/38* (2013.01);
(Continued)

(58) Field of Classification Search
CPC ...... C12M 23/42; C12M 23/22; C12M 23/34; C12M 23/38; C12M 23/46; C12M 29/00; C12M 41/44
See application file for complete search history.

(56) References Cited

U.S. PATENT DOCUMENTS 4,839,292 A * 6/1989 Cremonese ............ C12M 23/08
435/297.2
2004/0229383 A1* 11/2004 Vischer ............. H01L 21/67121
438/1
(Continued)

FOREIGN PATENT DOCUMENTS

CN 102124096 A 7/2011
CN 102858947 A 1/2013
(Continued)

OTHER PUBLICATIONS

Eric W. Esch et al., "Organs-on-chips at the frontiers of drug discovery", Nature Reviews Drug Discovery, published in Apr. 2015, vol. 14, issue 4, pp. 1-31, published by Nature Publishing Group, United Kingdom.
(Continued)

*Primary Examiner* — William H. Beisner
*Assistant Examiner* — Danielle B Henkel
(74) *Attorney, Agent, or Firm* — Fay Sharpe LLP

(57) ABSTRACT

A cell culture device includes a main body and a plug element. The main body includes a slot, an open groove and a fluid chamber. The open groove is connected with one side of the slot. The fluid chamber is disposed inside the main body and connected with another side of the slot. The plug element includes a first cell culture chamber and a first porous membrane. The first porous membrane is disposed at one side of the first cell culture chamber. The plug element is detachably plugged into the slot. When the plug element is plugged into the slot, the first cell culture chamber is communicated with the open groove to form an open space, and the open space and the fluid chamber are separated by the first porous membrane.

10 Claims, 25 Drawing Sheets
(3 of 25 Drawing Sheet(s) Filed in Color)

(52) U.S. Cl.
CPC ............ *C12M 23/46* (2013.01); *C12M 29/00* (2013.01); *C12M 41/44* (2013.01)

(56) References Cited

U.S. PATENT DOCUMENTS

| | | |
|---|---|---|
| 2017/0059555 A1* | 3/2017 | Iyer ........................ C12M 25/04 |
| 2017/0166853 A1* | 6/2017 | Ekeroth ................. C12M 25/06 |
| 2018/0080925 A1 | 3/2018 | Benam et al. |

FOREIGN PATENT DOCUMENTS

| | | |
|---|---|---|
| CN | 206319010 U | 7/2017 |
| WO | WO 2010057672 A1 | 5/2010 |

OTHER PUBLICATIONS

Bing-Syuan Ni et al., "Construction of a human lung tumor platform for tumor metastasis study", 65th TwIChE Annual Meeting, dated on Nov. 9-10, 2018, poster, Taiwan, R.O.C.

* cited by examiner

CELL CULTURE DEVICE AND CELL CULTURE SYSTEM

RELATED APPLICATIONS

This application claims priority to Taiwan Application Serial Number 107137237, filed Oct. 22, 2018, which is herein incorporated by reference.

BACKGROUND

Technical Field

The present disclosure relates to a cell culture device and a cell culture system. More particularly, the present disclosure relates to a cell culture device and a cell culture system which can effectively reduce the production costs and streamline operation steps.

Description of Related Art

According to the statistics of the Ministry of Health and Welfare, as of 2017, cancer has been the ten leading causes of death for 36 consecutive years. Many diagnosis data have confirmed that cancer metastasis is the main cause of death in patients. Cancer metastasis includes stages such as migration, intravasation, circulating, extravasation, and growth of secondary site. Reconstructing tumor microenvironments through the in vitro culture device for the cancer cells to simulate the interaction between the cancer cells and the normal cells is conducive to investigation of the mechanism of cancer metastasis.

However, conventional in vitro culture devices for the cancer cells are mostly integrally formed. The production process is complicated and difficult to operate, which causes a burden of production costs and labor costs. Besides, the conventional in vitro culture device for cancer cells can only simulate one specific stage of cancer metastasis. Thus it is necessary to prepare different in vitro culture devices for the cancer cells to investigate different stage of cancer metastasis, resulting in increase in research costs.

Therefore, how to improve the in vitro culture device is a goal of current industries and scholars. The improved in vitro culture device can be conducive to streamlining the production process and simplifying the operation methods, and can be used to simulate multiple stages of cancer metastasis, so as to reduce the research costs.

SUMMARY

According to one aspect of the present disclosure, a cell culture device includes a main body and a plug element. The main body includes a slot, an open groove, and a fluid chamber. The open groove is connected with one side of the slot. The fluid chamber is disposed inside the main body and connected with another side of the slot. The plug element includes a first cell culture chamber and a first porous membrane. The first porous membrane is disposed in one side of the first cell culture chamber. The plug element is detachably inserted in the slot, when the plug element is plugged into the slot, the first cell culture chamber is communicated with the open groove so as to form an open space, and the open space and the fluid chamber are separated by the first porous membrane.

According to another aspect of the present disclosure, a cell culture system includes a cell culture device and a pump. The cell culture device includes a main body and a plug element. The main body includes a slot, an open groove, a fluid chamber and two fluid gates. The open groove is connected with one side of the slot. The fluid chamber is disposed in the main body and connected with the other side of the slot. The two fluid gates are disposed at two sides of the fluid chamber, respectively. The plug element includes a first cell culture chamber and a first porous membrane. The first porous membrane is disposed at one side of the first cell culture chamber. The plug element is detachably plugged into the slot, when the plug element is plugged in the slot, the first cell culture chamber is communicated with the open groove so as to form an open space. The open space and the fluid chamber are separated by the first porous membrane. The pump is connected with the two fluid gates for cyclically flowing a fluid in the fluid chamber.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

The terms "first" and "second" are not used for indicating quality or other meanings but used for naming in the present disclosure. In addition, the "single culture" herein refers to culture for a single type of cell, not just for a single cell.

Cell Culture Device

Figure 1:
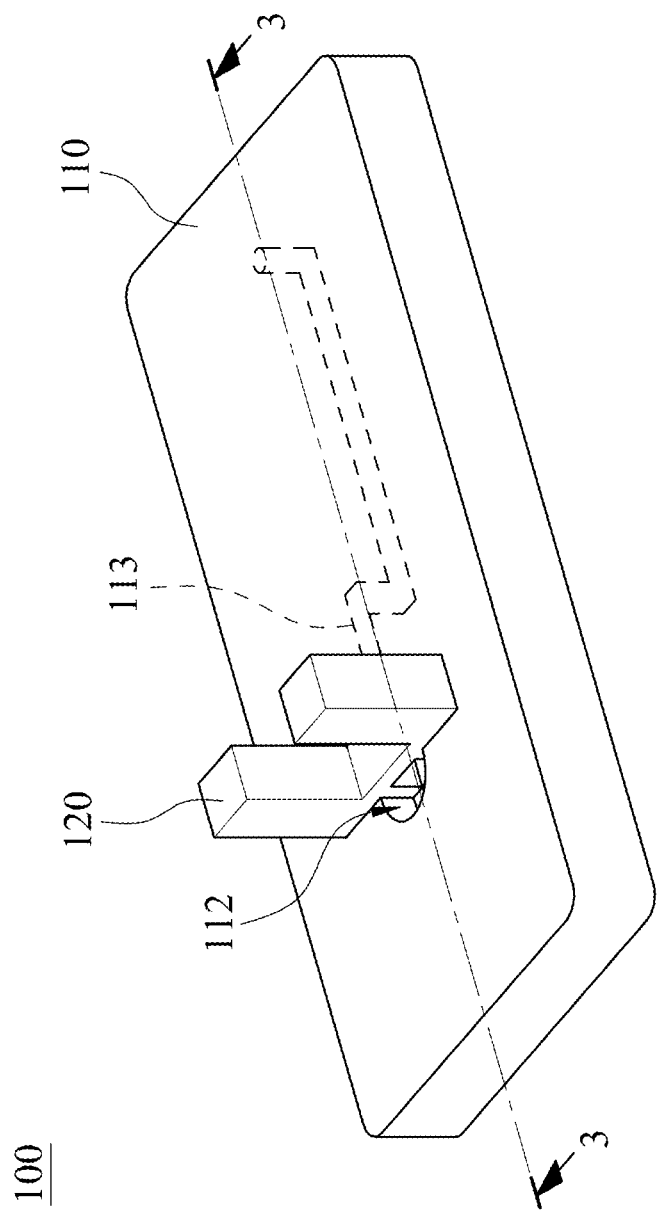
FIG. 1 is a three-dimensional view of a cell culture device according to one embodiment of the present disclosure.
Figure 2:
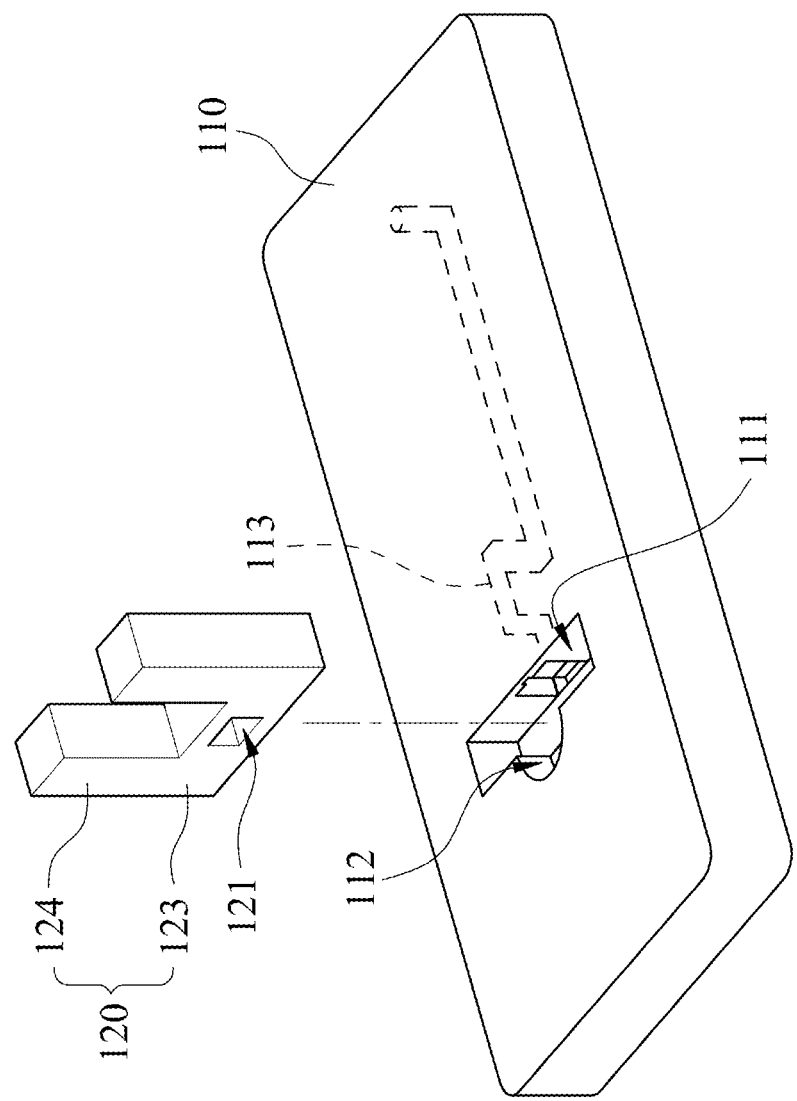
FIG. 2 is an exploded view of the cell culture device of FIG. 1.

Please refer to FIGS. 1 and 2. FIG. 1 shows a three-dimensional view of a cell culture device 100 according to one embodiment of the present disclosure. FIG. 2 shows an exploded view of the cell culture device 100 of FIG. 1. In FIGS. 1 and 2, the cell culture device 100 includes a main body 110 and a plug element 120.

In FIG. 2, the main body 110 includes a slot 111, an open groove 112 and a fluid chamber 113. The open groove 112 is connected with one side of the slot 111 (its reference numeral is omitted), and the fluid chamber 113 is disposed inside the main body 110, and the fluid chamber 113 is connected with another side of the slot 111 (its reference numeral is omitted), and the plug element 120 is detachably plugged in the slot 111.

Figure 3:
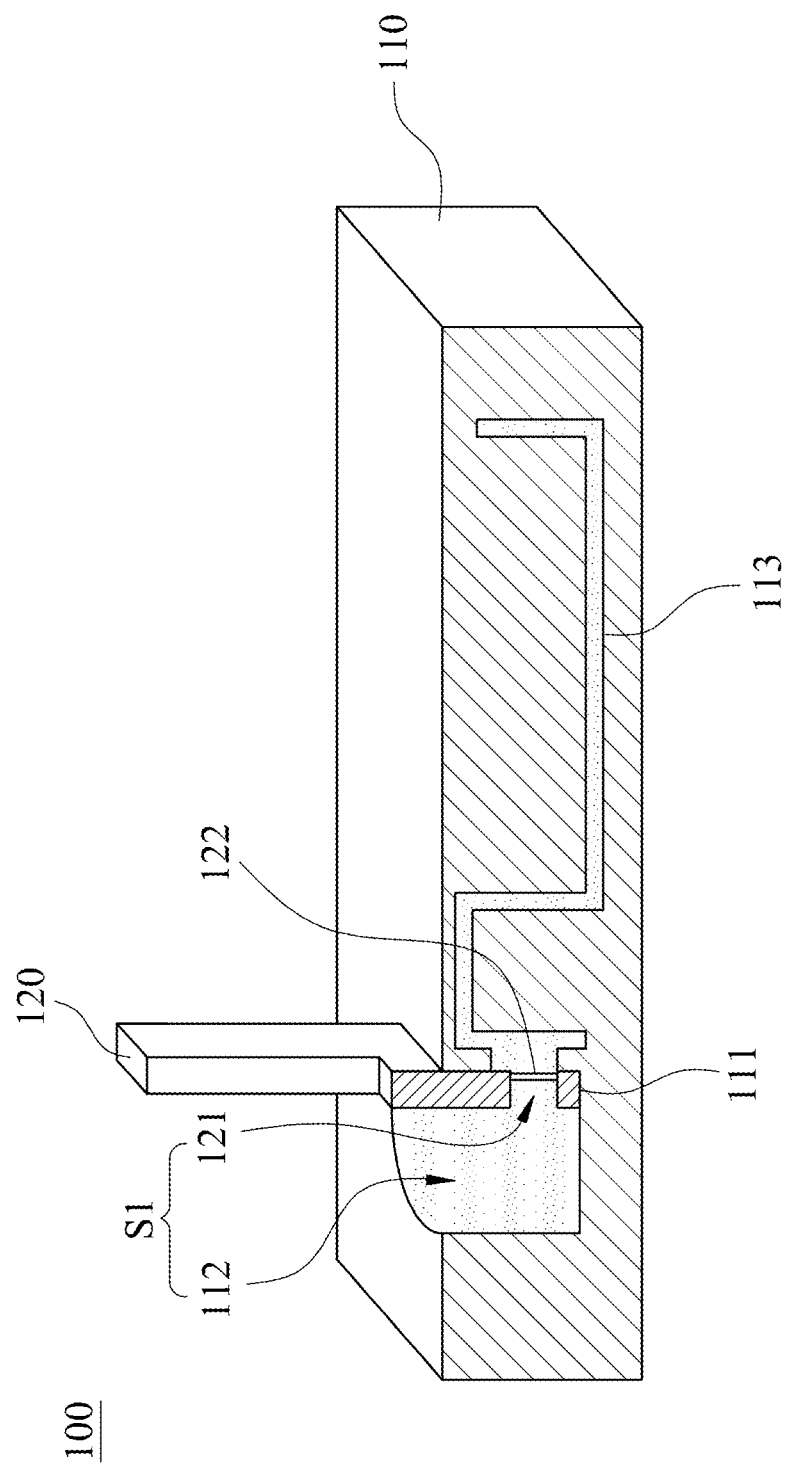
FIG. 3 is a cross-sectional view of the cell culture device taken along line 3-3 of FIG. 1.

FIG. 3 shows a cross-sectional view of the cell culture device 100 taken along line 3-3 of FIG. 1. In FIG. 3, the plug element 120 includes a first cell culture chamber 121 and a first porous membrane 122, and the first porous membrane 122 is disposed at one side of the first cell culture chamber 121. When the plug element 120 is plugged in the slot 111, the first cell culture chamber 121 is communicated with the open groove 112 so as to form an open space S1, and the open space S1 and the fluid chamber 113 are separated by the first porous membrane 122.

The cell culture device 100 can be used for culturing the cancer cells and simulating the tumor microenvironment. When performing different experiment, only the plug element 120 needs to be replaced (in other words, only the plug element 120 needs to be remanufactured), and the main body 110 can be reused. Therefore, the manufacturing process of the cell culture device 100 can be simplified, and the manufacturing costs can be reduced. Besides, during the experiment, the plug element 120 can be taken out to be observed without stopping the experiment. After finishing observation, the plug element 120 can be plugged back into the main body 110. Therefore, the operation method of the cell culture device 100 can be simplified, and the labor costs can be reduced.

Hereinafter, a fluid chamber side (its reference numeral is omitted) is used in specification to represent one side of the first porous membrane 122 toward the fluid chamber 113, and a culture chamber side (its reference numeral is omitted) is used in specification to represent one side of the first porous membrane 122 toward the first cell culture chamber 121.

For example, the cell culture device 100 can be applied to a static culture of single culture, wherein the 'static' refers to the fluid does not flow. In the static culture of single culture, a cell medium can be used as the fluid of the fluid chamber 113, and the cells are cultured in the first cell culture chamber 121 of the plug element 120 beforehand. The cell medium is filled in the fluid chamber 113 through the opening of the slot 111, and then the plug element 120 with the cells is plugged in the slot 111 of the main body 110 to observe the interaction between the cells of the culture chamber side and the cell medium of the fluid chamber side through the first porous membrane 122. In other embodiments, a fluid gate (not shown) can be formed on the main body 110, and the fluid gate is connected with the fluid chamber 113 to facilitate filling or replacing the cell medium in the fluid chamber 113. Besides, the cell medium can be added through the open groove 112 during culture to prevent the cells cultured in the first cell culture chamber 121 from dying due to exposure in the air.

For another example, the cell culture device 100 can be applied for static co-culture of different cells. In the static co-culture of different cells, the cell medium can be used as the fluid of the fluid chamber 113, and the first type of the cells is cultured in advance in one side of the first porous membrane 122 relatively to the first cell culture chamber 121 (that is the fluid chamber side, which can be regarded as culturing in the fluid chamber 113). Then, the second type of the cells is cultured at another side of the first porous membrane 122 facing the first cell culture chamber 121 (that is the culture chamber side, which can be regarded as culturing in the first cell culture chamber 121), and the cell medium is filled in the fluid chamber 113 from the opening of the slot 111. The plug element 120 culturing the first type of the cells and the second type of the cells is plugged in the slot 111 of the main body 110 to observe the interaction between the second type of the cells cultured in the culture chamber and the first type of the cells cultured in the fluid chamber side through the first porous membrane 122.

Figure 4:
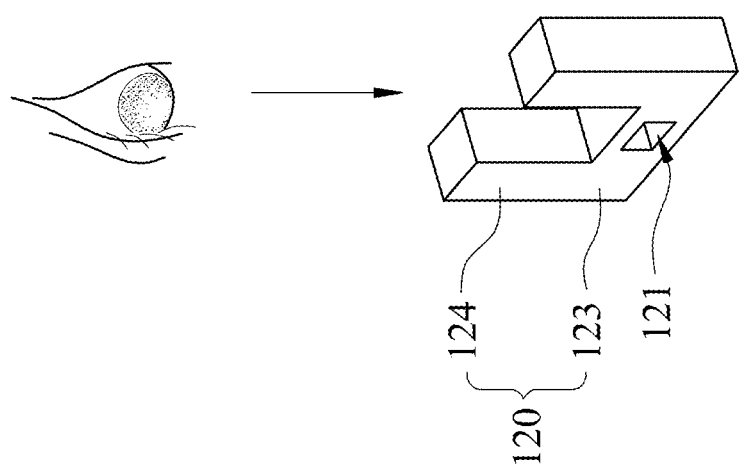
FIG. 4 is an observing schematic view of a plug element of FIG. 1.

Please refer to FIGS. 2 and 4. FIG. 4 shows an observing schematic view of the plug element 120 of FIG. 1. In FIGS. 2 and 4, the plug element 120 can include an inserting portion 123 and two extracting portions 124, wherein the inserting portion 123 is correspondingly plugged in the slot 111. Two extracting portions 124 are disposed at two sides of the inserting portion 123 respectively, so that the plug element 120 is U-shaped, wherein the first cell culture chamber 121 and the first porous membrane 122 are disposed at the inserting portion 123. Thereby, it is beneficial to detach the plug element 120 from the main body 110 for observation. Preferably, the inserting portion 123 can be a transparent material, and therefore it can further facilitate convenience of observation. In FIG. 4, when the plug element 120 is detached from the main body 110, the direction of the plug element 120 can be maintained (that is vertical to the direction of the main body 110). The cultured cells can be observed from the U-shaped groove, and the plug element 120 is plugged back into the main body 110 after finishing observation. In this way, the direction of the plug element 120 can be maintained consistently during the whole observation process, and the growth situation of the cells in the first cell culture chamber 121 is not easily interfered. Thus it is beneficial for maintaining the accuracy of the experiment result. Besides, the eyes (its reference numeral is omitted) of FIG. 4 represents the direction of observation, and the manner of observation is not limited to directly observation by naked eyes, and can be utilized, for example but not limited to, optical microscope-assisted observation.

In detail, the material of the first porous membrane 122 of the plug element 120 can be but not limited to polyethylene terephthalate (PET), and the material of the inserting portion 120 except the first porous membrane 122 can be but not limited to acrylic. In principle, any material that is biocompatible and non-toxic can be used as the material of the plug element 120.

The thickness of the first porous membrane 122 can be but not limited to 0.001 mm to 1 mm, and a pore size of the first porous membrane 122 can be but not limited to 0.1 μm to 100 μm. According to one embodiment of the present disclosure, the material of the first porous membrane 122 is PET, and the thickness of the first porous membrane 122 is 0.25 mm, and the pore size of the first porous membrane 122 is 8 μm. Therefore, the thickness and the pore size of the first porous membrane 122 can be flexibly adjusted by the cell culture device 100 of the present disclosure according to the cell type needed to culture and the experiment purpose.

The main body 110 and the plug element 120 can be made by the laser cut. Specifically, in the laser cut system (such as PLS 6.75, Arizona, USA), a two-dimensional design drawing can be drawn through the software (such as Solid Edge, Siemens PLM Software), and then the two-dimensional design drawing is exported to cut to obtain a plurality of layered structures. Finally, the plurality of the layered structures are stacked and bonded to obtain the main body 110 and the plug element 120 of the present disclosure.

Figure 5:
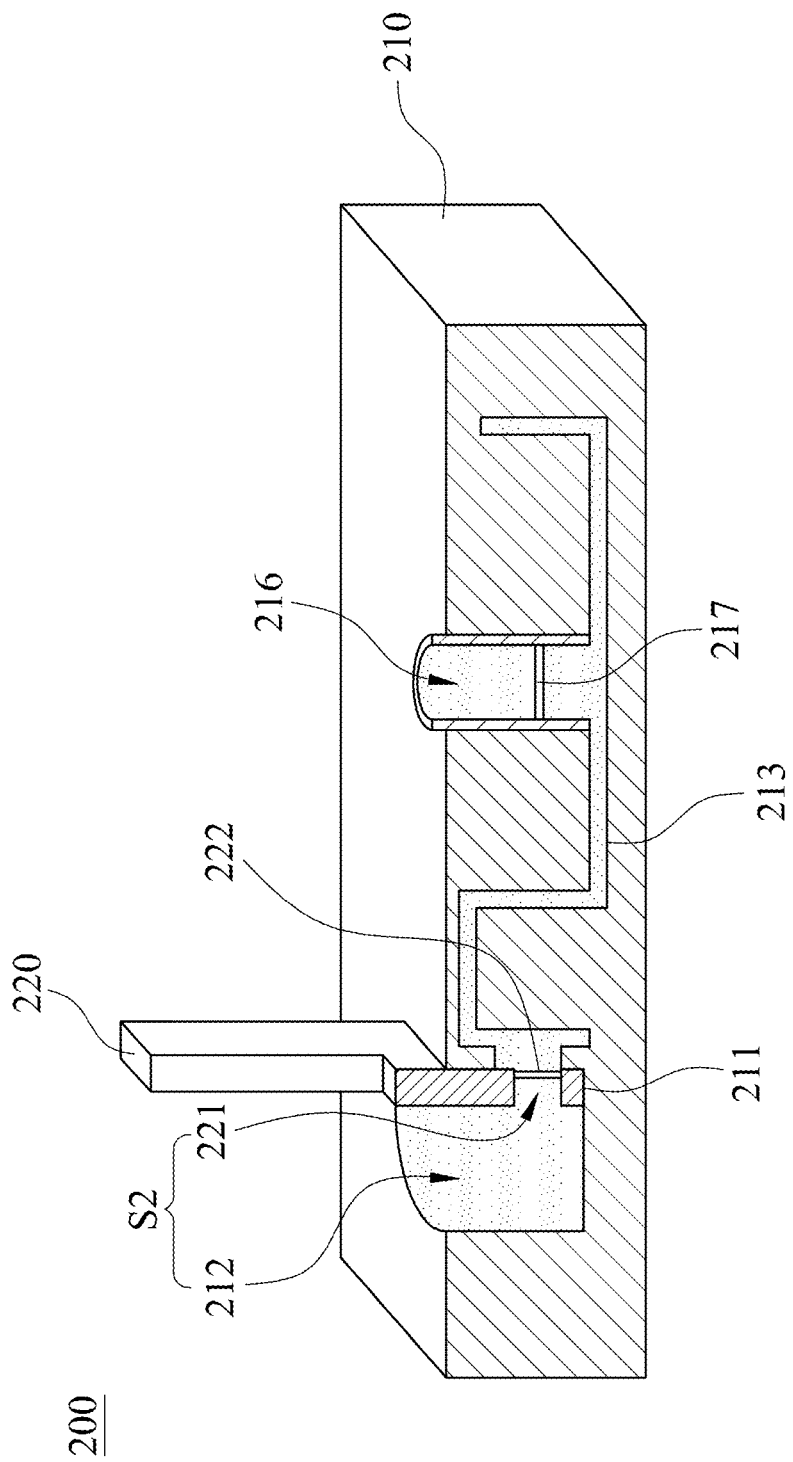
FIG. 5 is a cross-sectional view of a cell culture device according to another embodiment of the present disclosure.
Figure 6:
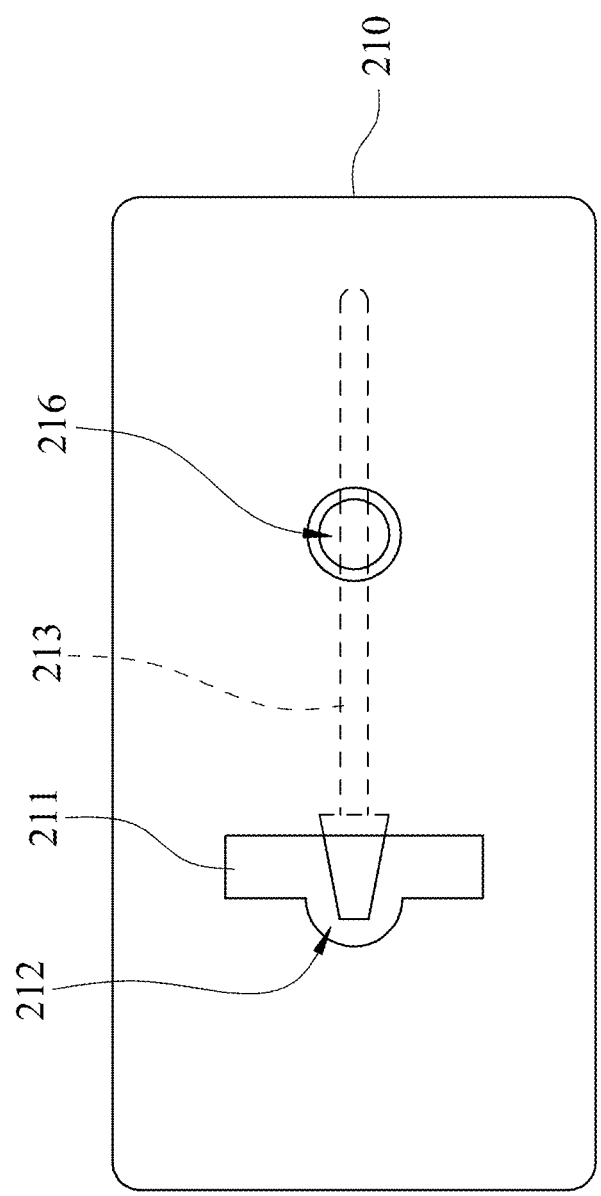
FIG. 6 is a top view of a main body of FIG. 5.

Please refer to FIGS. 5 and 6. FIG. 5 shows a cross-sectional view of a cell culture device 200 according to another embodiment of the present disclosure. FIG. 6 shows a top view of a main body 210 of FIG. 5. The cross-section position of FIG. 5 is same as FIG. 3. In FIGS. 5 and 6, the cell culture device 200 includes the main body 210 and a plug element 220.

FIG. 5 shows the main body 210 including a slot 211, an open groove 212 and a fluid chamber 213. The open groove 212 is connected with one side of the slot 211 (its reference numeral is omitted), the fluid chamber 213 is disposed in the main body 210, the fluid chamber 213 is connected with another side of the slot 211 (its reference numeral is omitted), and the plug element 220 is detachably plugged in the slot 211. The plug element 220 includes a first cell culture chamber 221 and a first porous membrane 222, and the first porous membrane 222 is disposed at one side of the first cell culture 221. When the plug element 220 is plugged in the slot 211, the first cell culture chamber 221 is communicated with the open groove 212 so as to form an open space S2, and the open space S2 and the fluid chamber 213 are separated by the first porous membrane 222. The cell culture device 200 further includes a second cell culture chamber 216 and a second porous membrane 217, and the second cell culture 216 and the fluid chamber 213 are separated by the second porous membrane 217. The second cell culture chamber 216 and the second porous membrane 217 are disposed as a detachable round tube element (its reference numeral is omitted) of the embodiment of the present disclosure, but not limited thereto.

For example, the cell culture device 200 can be applied for a static co-culture of multiple cells. In detail, the first type of the cells are cultured in a fluid chamber side of the first porous membrane 222 in advance, the second type of the cells are cultured in the culture chamber side of the first porous membrane 222, and a third type of the cells are cultured at the second porous membrane 217 facing one side of the second cell culture chamber 216 (that is cultured in the second cell culture 216) in advance. A cell medium is filled in the fluid chamber 213, and the plug element 220 culturing the first type of the cells and the second type of the cells and the round tube element culturing the third type of the cells are plugged in the main body 210 to observe the interaction among the second type of the cells cultured in the culture chamber side, the first type of the cells cultured in the fluid chamber side, the third type of the cells and the cell medium through the first porous membrane 220 and the second porous membrane 217. In other embodiment, the number of the cell culture chamber and the porous membrane can be increased according to actual needs, and it is advantageous to co-culture a variety of the cells. For example, a third cell culture chamber, a third porous membrane, a fourth cell culture chamber and a fourth porous membrane can be increased. The conventional in vitro culture device for observing the cancer cells is usually used to co-culture of the cancer cells with another normal human cells. However, the cell culture device of the present disclosure can used to co-culture the cancer cells with various other cells, such as epithelial cells and fibroblasts, and it can more realistically simulate the human tumor microenvironment.

The rest details of the cell culture device 200 are the same as that shown in the cell culture device 100 of FIGS. 1 and 3 without causing any inconsistencies, and thus it is not illustrated any further.

Figure 7:
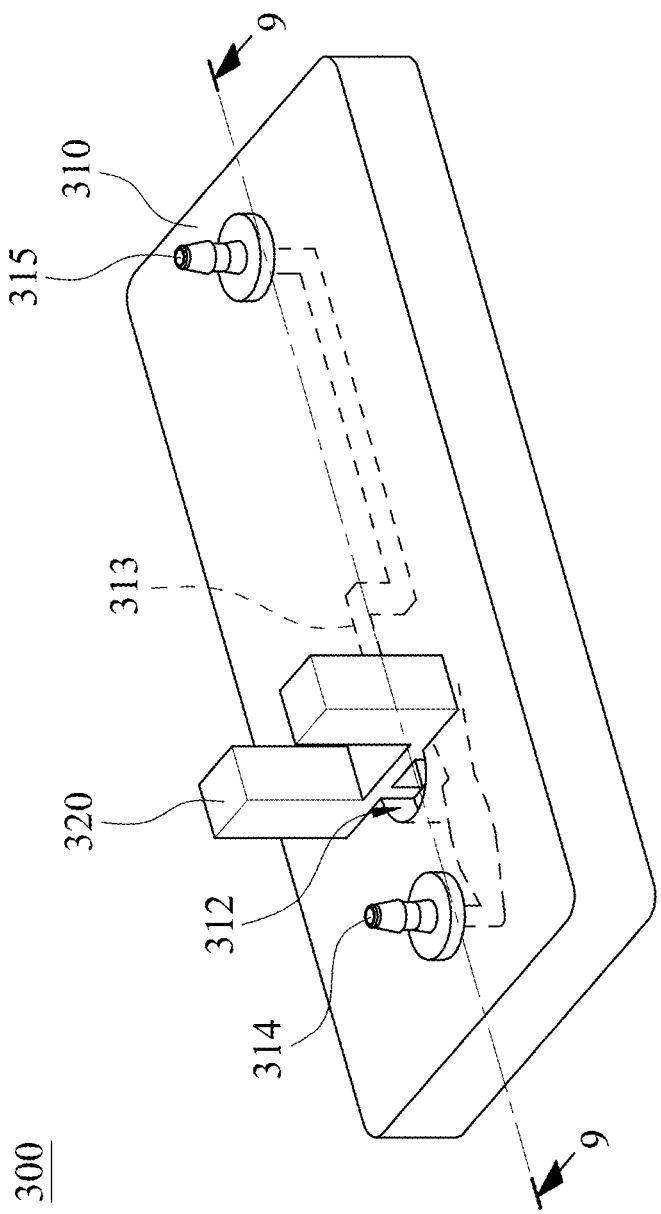
FIG. 7 is a three-dimensional view of a cell culture device according to still another embodiment of the present disclosure.
Figure 8:
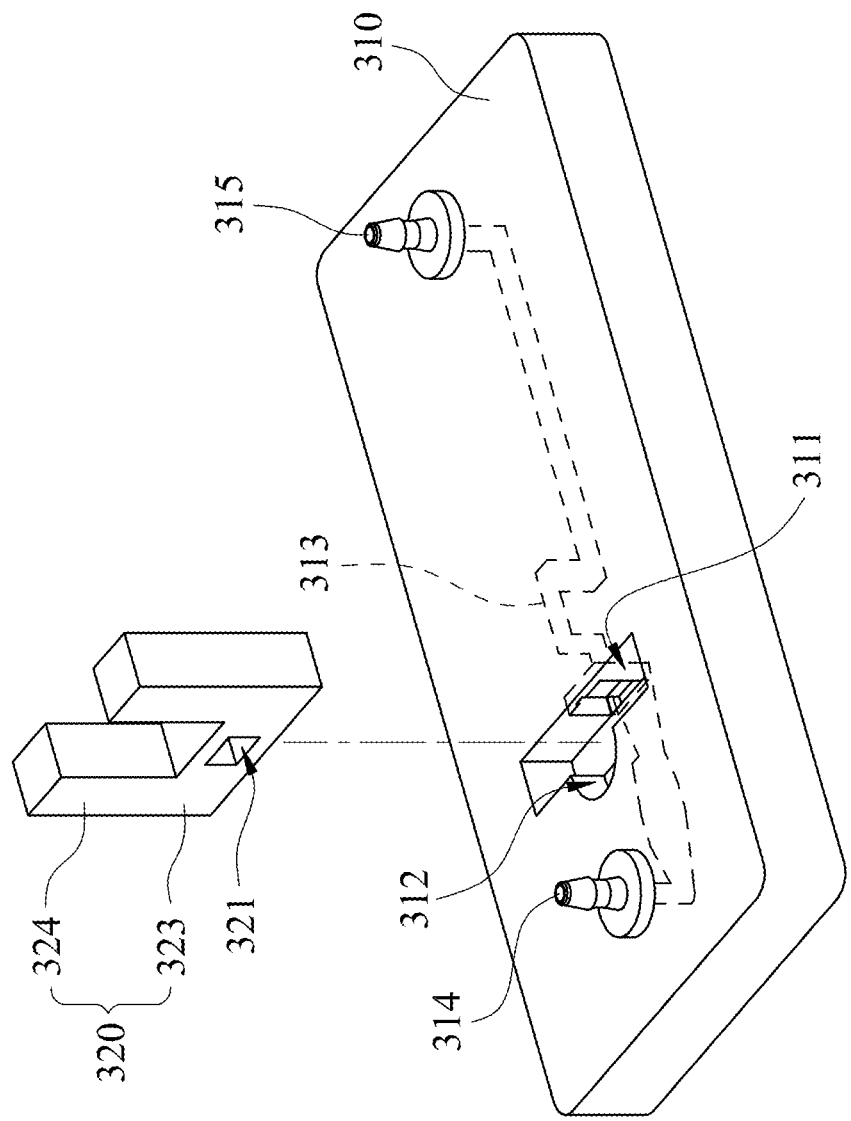
FIG. 8 is an exploded view of the cell culture device of FIG. 7.

Please refer to FIGS. 7 and 8. FIG. 7 shows a three-dimensional view of a cell culture device 300 according to still another embodiment of the present disclosure, and FIG. 8 shows an exploded view of the cell culture device 300 of FIG. 7. In FIGS. 7 and 8, the cell culture device 300 includes a main body 310 and a plugged element 320.

FIG. 8 shows the main body 310 including a slot 311, an open groove 312, a fluid chamber 313, a fluid gate 314 and a fluid gate 315. The open groove 312 is connected with one side of the slot 311 (its reference numeral is omitted), and the fluid chamber 313 is disposed inside the main body 310, and the fluid chamber 313 is connected with another side of the slot 311 (its reference numeral is omitted), and the fluid gate 314 and the fluid gate 315 are disposed at two sides of the fluid chamber 313, respectively. The plug element 320 is detachably plugged in the slot 311. The plug element 320 can include an inserting portion 323 and two extracting portions 324, wherein the inserting portion 323 is correspondingly plugged in the slot 311, and two extracting portions 324 are disposed at two sides of the inserting portion 323, respectively, so that the plug element 320 is U-shaped.

Figure 9:
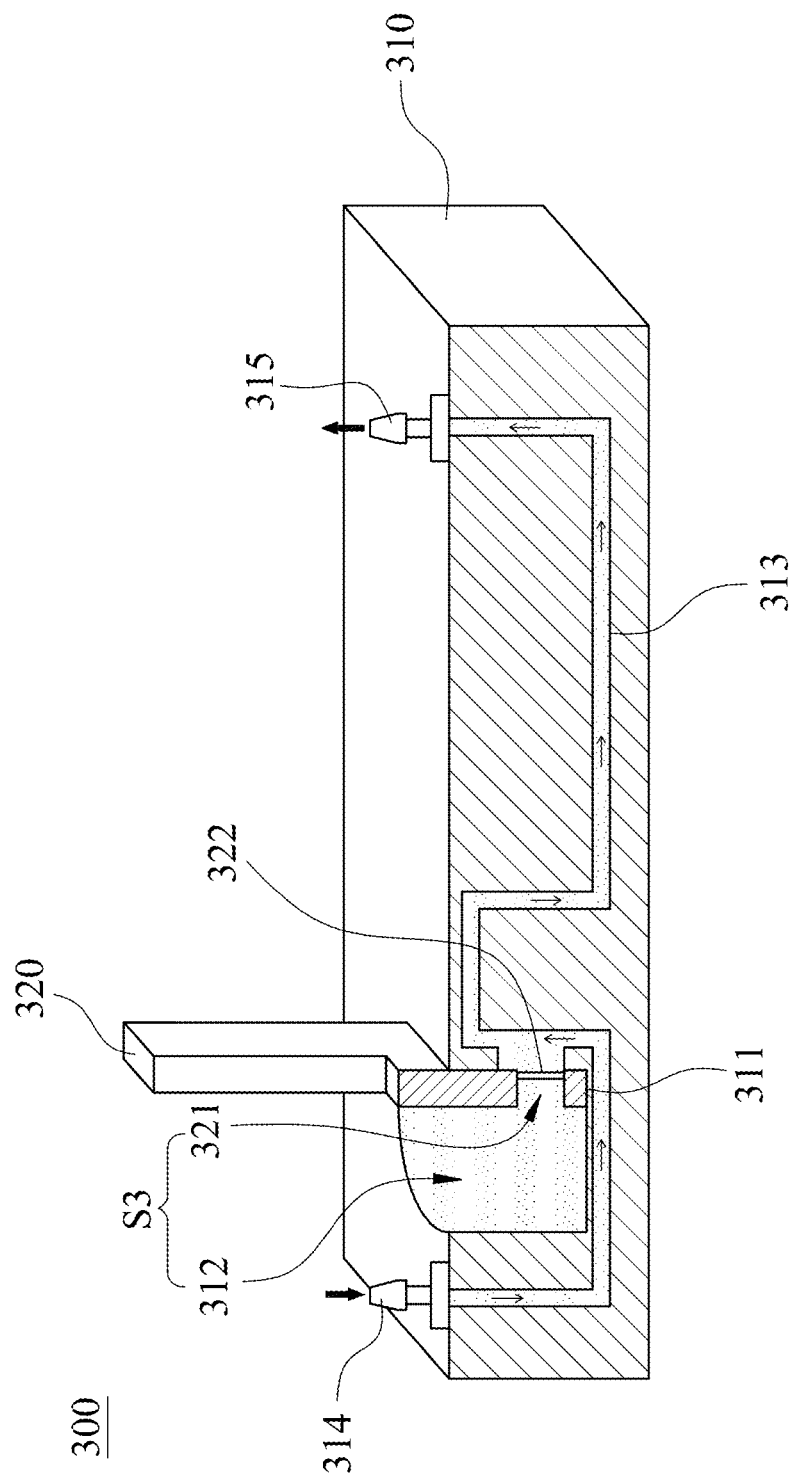
FIG. 9 is a cross-sectional view of the cell culture device taken along line 9-9 of FIG. 7.

FIG. 9 shows a cross-sectional view of the cell culture device 300 taken along line 9-9 of FIG. 7. In FIG. 9, the plug element 320 includes a first cell culture chamber 321 and a first porous membrane 322, and the first porous membrane 322 is disposed at one side of the first cell culture chamber 321. When the plug element 320 is plugged in the slot 311, the first cell culture chamber 321 is communicated with the open groove 312 so as to form an open space S3, and the open space S3 and the fluid chamber 313 are separated by the first porous membrane 322.

The cell culture device 300 can be used for culturing the cancer cells and simulating the tumor microenvironment. When performing different experiment, only the plug element 320 needs to be replaced (in other words, only the plug element 320 needs to be remanufactured), and the main body 310 can be reused for simplifying the manufacturing process of the cell culture device 300 and reducing the manufacturing costs. Besides, during the experiment, the plug element 320 can be taken out to be observed without stopping the experiment. After finishing observation, the plug element 320 can be plugged back into the main body 320. It is beneficial for simplifying the operation method of the cell culture device 300 and reducing the labor costs.

For example, the cell culture device 300 can be applied for dynamic culture of single culture, wherein the term 'dynamic' refers to a circulation flow generated by a fluid. In detail, the fluid can be circulated in the fluid chamber 313 to form a dynamic environment by a power such as pump (not shown) connected with the fluid gate 314 and the fluid gate 315. The fluid chamber 313 can be regarded as a kind of flow channel, and the cell medium can be regarded as a fluid. The plug element 320 with the cells is plugged in the slot 311 of the main body 310 to observe the interaction between the cells of the culture chamber side and the cell medium of the flow chamber side through the first porous membrane 322 in the dynamic environment.

For another example, the cell culture device 300 can be applied to the dynamic cell co-culture, and the fluid can be circulated in the fluid chamber 313 to form a dynamic environment by the power such as pump (not shown) connected with the fluid gate 314 and the fluid gate 315. Then, the plug element 320 culturing the first type of the cells and the second type of the cells (the detail please refer to static cell co-culture) is plugged in the slot 311 of the main body 310 to observe the interaction among the second type of the cells of the culture chamber side, the first type of the cells of the fluid chamber side and the cell medium through the first porous membrane 322 in the dynamic environment. Thereby, it can simulate the pressure and the shear stress formed by blood circulation to more realistically simulate human tumor microenvironment.

In FIG. 9, arrows represent the direction of fluid flow. The fluid enters the fluid chamber 313 through the fluid gate 314, flows through the lower portion of the first cell culture chamber 321, contacts upward with the first porous membrane 322, flows out through the fluid gate 315, and circulates through this path. According to one embodiment of the present disclosure, the flow rate can be 0.75 mm/s to simulate the flow rate of blood in the blood capillary, but not limited thereto.

Other details of the cell culture device 300 can be the same as the cell culture device 100 of FIGS. 1 and 3 without causing any inconsistencies, and thus it is not illustrated any further.

Figure 10:
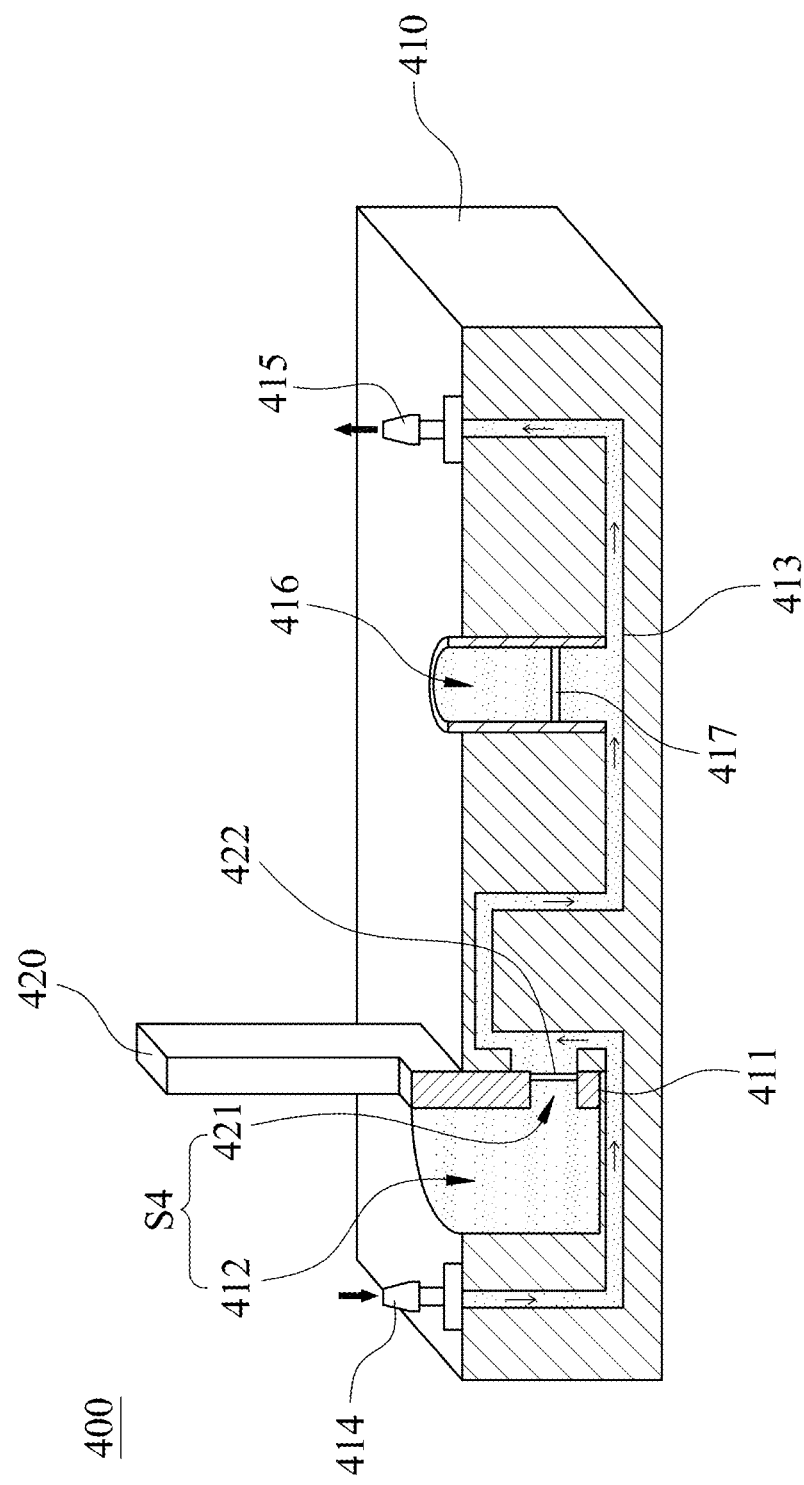
FIG. 10 is a cross-sectional view of a cell culture device according to yet another embodiment of the present disclosure.
Figure 11:
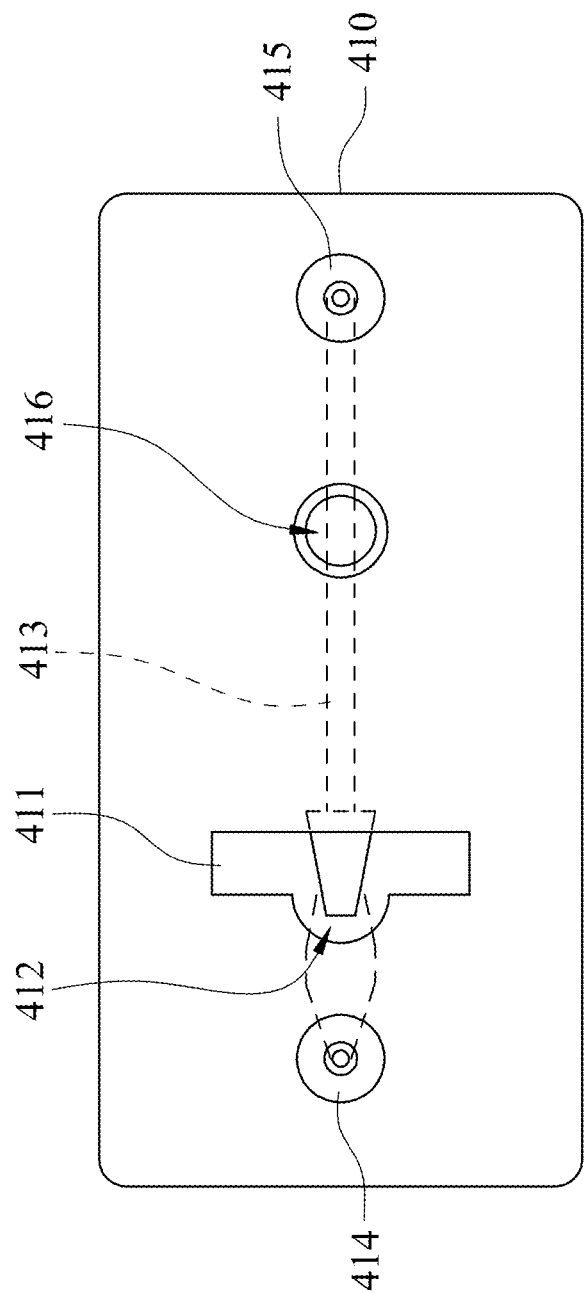
FIG. 11 is a top view of a main body of FIG. 10.

Please refer to FIGS. 10 and 11. FIG. 10 shows a cross-sectional view of a cell culture device 400 according to yet another embodiment of the present disclosure, and FIG. 11 shows a top view of a main body 410 of FIG. 10, wherein the cross-section position of FIG. 10 is same as the FIG. 3. In FIGS. 10 and 11, the cell culture device 400 includes the main body 410 and a plugged element 420.

In FIG. 10, the main body 410 includes a slot 411, an open groove 412, a fluid chamber 413, a fluid gate 414 and a fluid gate 415. The open groove 412 is connected with one side of the slot 411 (its reference numeral is omitted), the fluid chamber 413 is disposed inside the main body 410, the fluid chamber 413 is connected with another side of the slot 411 (its reference numeral is omitted), and the fluid gate 44 and the fluid gate 415 are disposed at two sides of the fluid chamber 413, respectively. The plug element 420 is detachably plugged in the slot 411. The plug element 420 includes a first cell culture chamber 421 and a first porous membrane 422, and the first porous membrane 422 is disposed at one side of the first cell culture 421. When the plug element 420 is plugged in the slot 411, the first cell culture chamber 421 is communicated with the open groove 412 so as to form an open space S4, and the open space S4 and the fluid chamber 413 are separated by the first porous membrane 422. The cell culture device 400 further includes a second cell culture chamber 416 and a second porous membrane 417, and the second cell culture 416 and the fluid chamber 413 are separated by the second porous membrane 417. The second cell culture chamber 416 and the second porous membrane 417 are disposed as a detachable round tube element (its reference numeral is omitted) of the embodiment of the present disclosure, but not limited thereto.

For example, the cell culture device 400 can be applied for dynamic co-culture of multiple cultures, and the fluid can be circulated in the fluid chamber 413 to form a dynamic environment by the power such as pump (not shown) connected with the fluid gate 414 and the fluid gate 415. In detail, the first type of the cells and the second type of the cells can be cultured at the culture chamber side of the first porous membrane 422, and the third type of the cells are cultured at one side of a second porous membrane 417 facing a second cell culture chamber 416 (in other words, cultured in the second cell culture chamber 416) in advance. A cell medium is filled in the fluid chamber 413, and the plug element 420 culturing the first type of the cells, the second type of the cells and the round tube element culturing the third type of the cells are plugged in the main body 410 to observe the interaction among the second type of the cells of culture chamber side, the first type of the cells cultured in the fluid chamber side, the third type cultured in the cells and the cell medium through the first porous membrane 422 and the second porous membrane 417 in the dynamic environment. Thereby, the cell culture device 400 of the present disclosure can be used to simulate the pressure and the shear stress formed by blood circulation, and can also be used to co-culture of the cancer cells with various other cells, such as epithelial cells, fibroblasts, and it can more realistically simulate the human tumor microenvironment.

Other details of the cell culture device 400 can be the same as the cell culture device 100 of FIGS. 1 and 3, can also be the same as the cell culture device 200 without causing any inconsistencies, and thus it is not illustrated any further.

Cell Culture System

Figure 12:
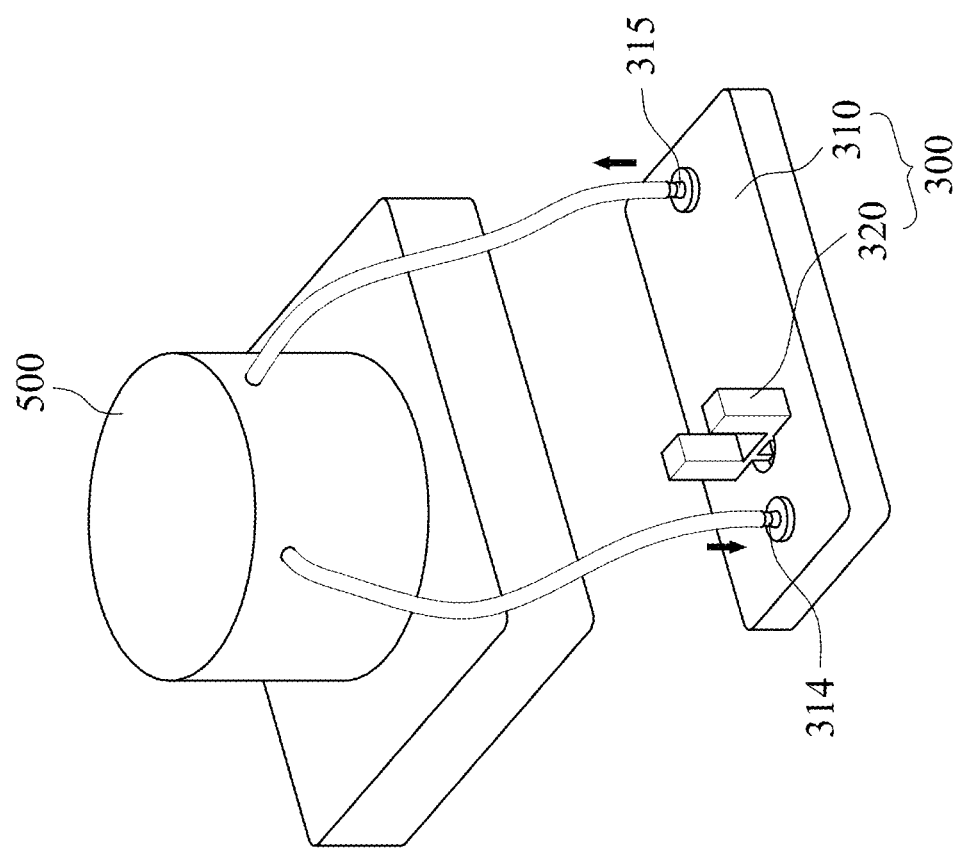
FIG. 12 is a three-dimensional view of a cell culture system according to one embodiment of the present disclosure.

FIG. 12 shows a three-dimensional view of a cell culture system 10 according to one embodiment of the present disclosure. In FIG. 12, the cell culture system 10 includes a cell culture device 300 and a pump 500. The pump 500 is connected with a fluid gate 314 and a fluid gate 315 of a main body 310, and the fluid (not shown) can be circulated in the fluid chamber 313 (FIG. 9). Please refer to the above for the cell culture device 300. Preferably, the pump 500 can be a peristaltic pump.

The cell culture system 10 can be applied to dynamic culture of single culture and dynamic co-culture of various cells. Besides, the cell culture system 10 can be used to simulate a plurality of stages of cancer metastasis, such as migration stage, intravasation stage, circulating stage and growth of secondary site stage. By contrast, the conventional in vitro cell culture device of cancer cells only can be applied to simulate one of the specific stages. Therefore, the cell culture system 10 can reduce the labor costs.

Figure 13:
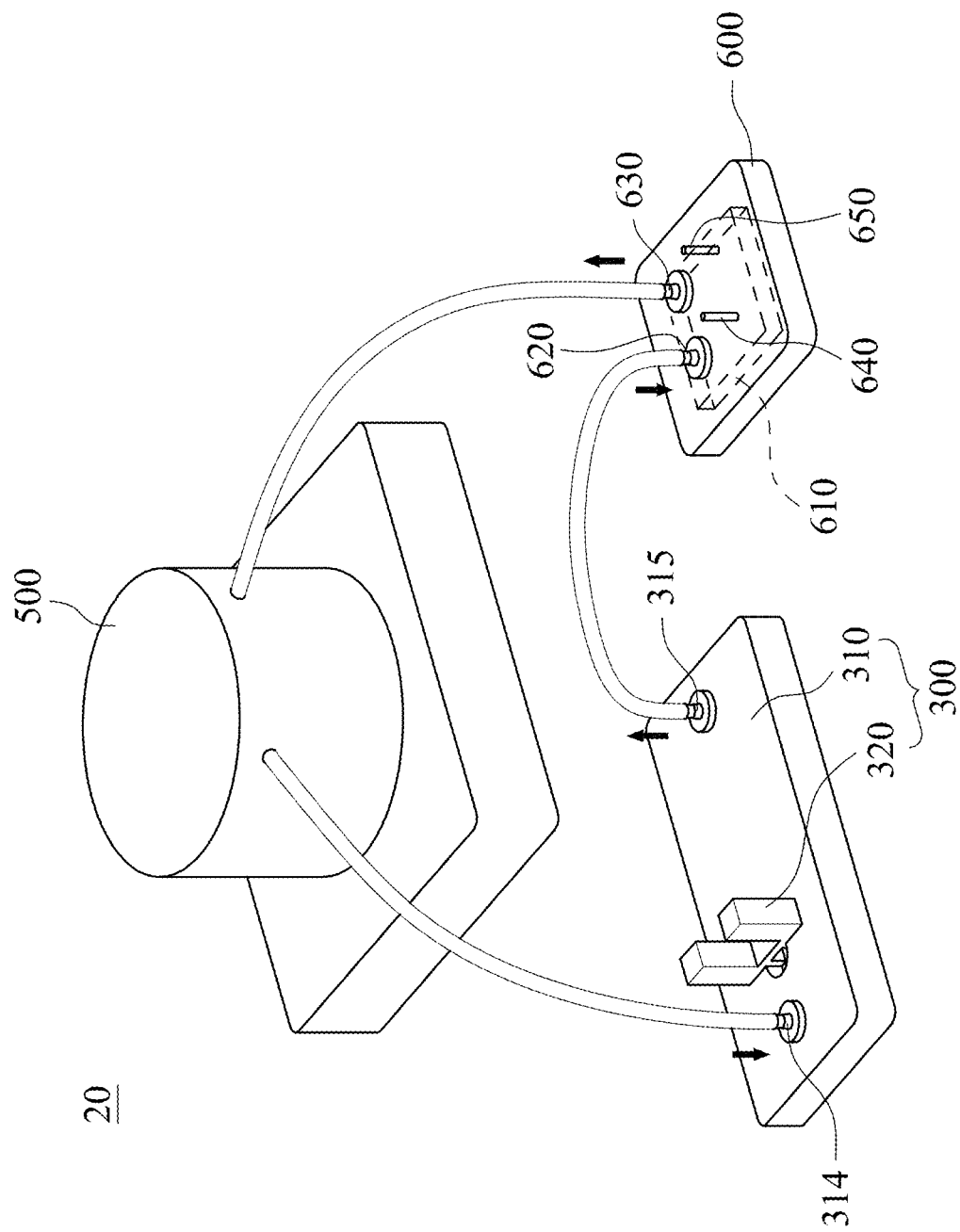
FIG. 13 is a three-dimensional view of a cell culture system according to another embodiment of the present disclosure.

FIG. 13 shows a three-dimensional view of a cell culture system 20 according to another embodiment of the present disclosure. In FIG. 13, the cell culture system 20 includes a cell culture device 300, a pump 500 and a fluid container 600. The fluid container 600 includes a fluid accommodation space 610, a fluid exchanging port 620 and a fluid exchanging port 630. The fluid exchanging port 620 and the fluid exchanging port 630 of the fluid container 600 is connected with the fluid accommodation space 610, wherein the pump 500 is connected with the fluid exchanging port 630 of the fluid container 600 and the fluid gate 314 of the main body 310, respectively, and the fluid exchanging port 620 of the fluid container 600 is connected with the fluid gate 315 of the main body 310, and the fluid (not shown) can be circulated in the fluid chamber 313 and the fluid accommodation space 610.

Compared to the cell culture system 10 of FIG. 12, the pump 500 of the cell culture system 20 is connected with the fluid gate 315 of the main body 310 through the fluid container 600, in other words, the connection method of the pump 500 and the fluid gate 315 of the main body 310 is indirect connection. During the actual operation, whether the fluid container 600 is used to increase the capacity of the fluid can be determined according to the accommodation capacity of the fluid chamber 313 of the main body 310.

In FIG. 13, the fluid container 600 further includes an outlet 640 and an inlet 650, and the outlet 640 and the inlet 650 are connected with the fluid accommodation space 610, respectively. The inlet 650 can be used to inject other ingredients like cytokines to adjust the condition of the cell culture, or can be used to replace fresh fluid. To balance the pressure during the operation, the inlet 650 is usually closed and only opened when the ingredient of the fluid needs to be adjusted or renewed. The outlet 640 can be used to sample or discharge the spent fluid, so that the outlet 640 is also closed during the operation.

Besides, arrows in FIGS. 12 and 13 represent the direction of fluid flow, but the flow direction of the fluid can be flexibly adjusted according to realistic need and not limited thereto. The cell culture device 300 in cell culture system 10 or in the cell culture system 20 can be replaced with the cell culture device 400 in the cell culture system of other embodiments. Thereby, the cell culture system can be applied to dynamic co-culture of multi-cells.

The Result of Culturing Cancer Cells

In the following experiment, the cell culture system needs to be sterilized before each experiment, including washed with 30% of hydrogen peroxide solution for at least 3 hours, washed with sterilized water, immersed in sterilized water for overnight, and then washed with phosphate buffered saline (PBS) for at least 3 hours and sterilized by ultraviolet light overnight.

The cells used in the following experiment include A549 cells, A549 cells with green fluorescent protein expression (A549/GFP) and human pulmonary microvascular endothelial cells (HPMECs). The ingredients of A549/GFP cells medium for culturing A549 cells and A549/GFP cells are 89% DMEM culture medium (25 mM), 10% fetal bovine serum (FBS) and 1% Penicillin/Streptomycin Solution (P/S), and the ingredients of endothelial cells medium for culturing HPMECs cells are 93% endothelial cell medium, 5% FBS, 1% P/S and 1% endothelial cell growth supplement. When co-culturing A549/GFP cells and HPMECs cells, the cell mediums are 50% A549/GFP cells medium and 50% endothelial cells medium, wherein the percentage of this paragraph refers to the volume percentage.

In the following experiment, the time is defined as follows. The time point of the cells are seeded on the porous membrane of the plug element, and placed into the cell culture incubator to make the cells attached on the porous membrane is defined as day 0. After 1 day, the time point of the cells attached on the porous membrane is defined as day 1, and other days have the same definition.

In the following experiment, static means that the pump is turned off, and dynamic means that the pump is turned on. The spindle rate of the pump is 2.3 RPM, so that the flow rate of the fluid is 0.75 mm/s to simulate the flow rate of the blood in the human blood capillary.

Two-Dimensional Cell Culture of A549 Cells

Experiment 1.1

Figure 14:
FIG. 14 shows a staining result of A549 cells in two-dimensional cell culture.

The experiment is carried out the plug element 320 of the cell culture device 300 in FIG. 7. First, the A549 cells are seeded on the first porous membrane 322 of the plug element 320 with $4 \times 10^4$ cells/ml, and cell staining is performed on the third culturing day to observe the survival condition of A549 cells. Please refer to FIG. 14, which shows a staining result of A549 cells in two-dimensional cell culture. In FIG. 14, the length of the scale represents 100 μm. In FIG. 14, the A549 cells are still survival on the first porous membrane 322 of the plug element 320 after three days, and it indicates that the plug element 320 of the present disclosure is biocompatible for culturing cells.

Two-Dimensional Cell Culture of A549/GFP Cells

Experiment 2.1 Single Culture of A549/GFP Cells

Figure 15A:
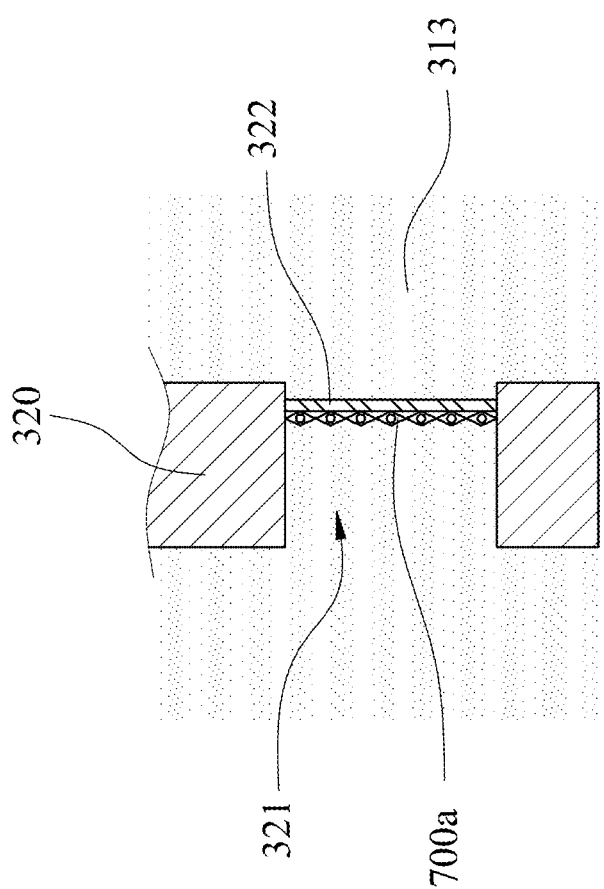
FIG. 15A is a partial enlargement schematic view of a single culture in two-dimensional cell culture using the cell culture device according to still another embodiment of the present disclosure.
Figures 16A, 16B:
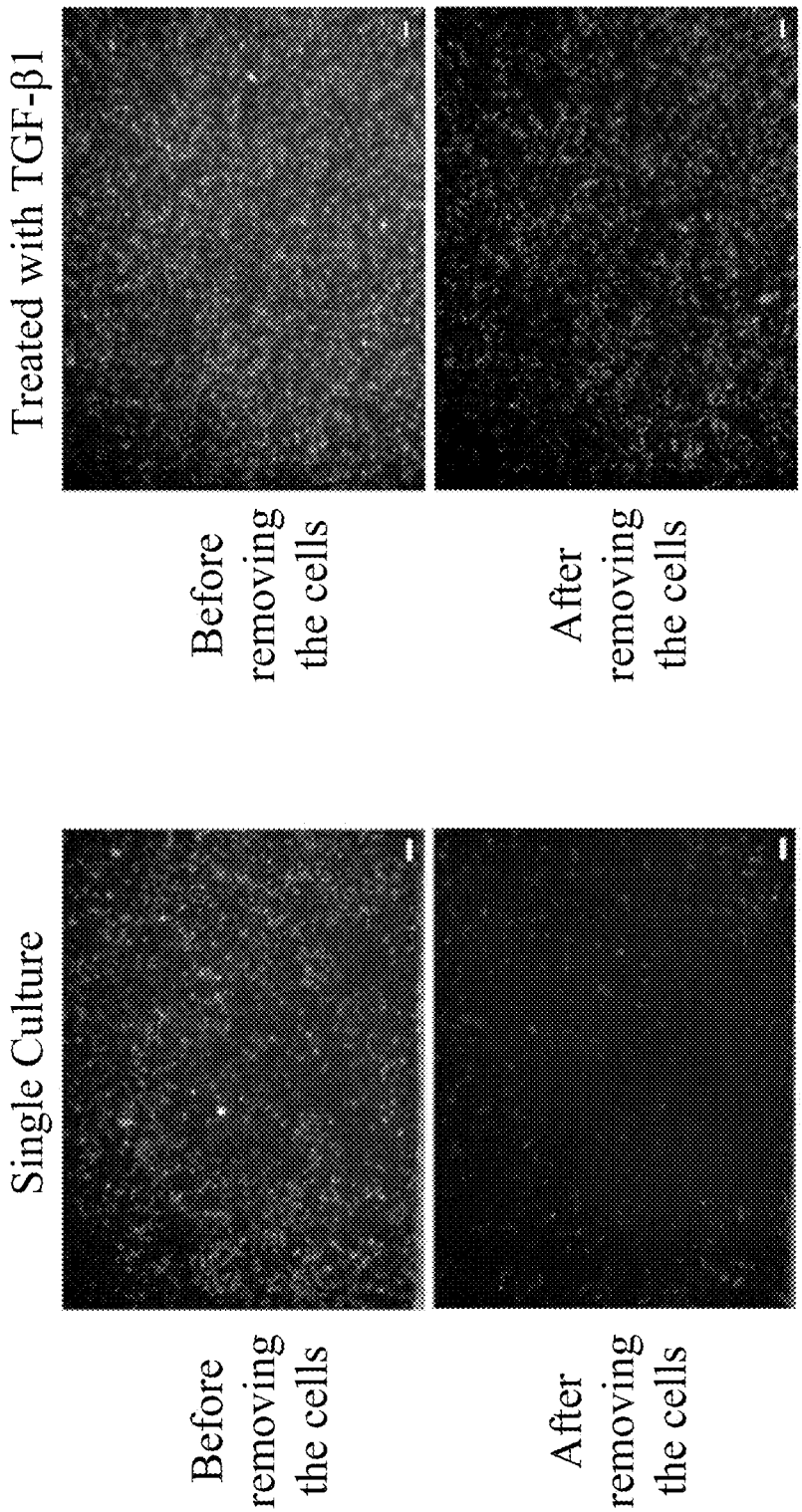
FIGS. 16A, 16B and 16C are microscopy images of A549/GFP cells in two-dimensional cell culture.

Please refer to FIG. 15A showing a partial enlargement schematic view of a single culture in two-dimensional cell culture using the cell device 300 according to still another embodiment of the present disclosure. In FIG. 15A, cells 700a are attached on the culture chamber side of the first porous membrane 322 of the plug element 320. In experiment 2.1, the cells 700a are A549/GFP cells, and the cell culture system 20 of FIG. 13 is used for the cell culture. Specifically, the plug element 320 is extracted from the main body 310, and then A549/GFP cells are seeded in the first porous membrane 322 of the plug element 320 with $1.6 \times 10^5$ cells/ml. After A549/GFP cells attached on the first porous membrane 322, the plug element 320 is plugged back into the main body 310, and cell culture is carried out in the dynamic condition to observe the distribution of A549/GFP cells on the first porous membrane 322, thereby inferring the condition of A549/GFP cells migrating from the culture chamber side to the fluid chamber side. Please refer to FIG. 16A showing microscopy images of single culture of A549/GFP cells in two-dimensional cell culture, and the scale bar represents 100 μm. The upper picture is the cell image of before removing the cells from the culture chamber side of the first porous membrane 322 with the cotton swab on the third day of culture, and the lower picture is the cell image of after removing the cells from the culture chamber side of the first porous membrane 322 with the cotton swab on the third day of culture, wherein A549/GFP cells that can be removed by the cotton swab represent cells with metastatic potential. The migration area percentage of A549/GFP cells on the third day can be calculated by the software of Image J for image analysis, and the calculation formula is shown below:

Migration area percentage (%)=($A3/A_0$)×100%, wherein $A_0$ is the area that no cell grows before removing the cells from the culture chamber side of the first porous membrane 322 with the cotton swab on the third day (referred to as before removal), and A3 is the area that no cell grows after removing the cells from the culture chamber side of the first porous membrane 322 with the cotton swab on the third day. After calculating, the migration area percentage of single culture of A549/GFP cells is 19.2%, and the standard deviation is 3.5% (n=3).

Experiment 2.2 Single Culture of A549/GFP Cells Treated with TGF-β1

The Difference Between Experiment 2.2 and the Experiment 2.1 is that 5 ng/mL recombinant human TGF-β1 (protein Human Cell-expressed) protein (R&D Systems, USA) is added in the cell medium every day. Please refer to FIG. 16B showing microscopy images of single culture of A549/GFP cells treated with TGF-β1 in two-dimensional cell culture, and the scale bar represents 100 μm. The upper picture is the cell image of before removing the cells from the culture chamber side of the first porous membrane 322 with the cotton swab on the third day, and the lower picture is the cell image of after removing the cells from the culture chamber side of the first porous membrane 322 with the cotton swab on the third day. The migration area percentage of A549/GFP cells on the third day can be calculated by combing with the software of Image J for image analysis, and the calculation formula is shown above, and will not repeat. After calculating, the migration area percentage of single culture of A549/GFP cells treated with TGF-β1 is 37.6%, and the standard deviation is 0.5% (n=3).

Experiment 2.3 Co-Culture of A549/GFP Cells and HPMECs Cells

Figure 15B:
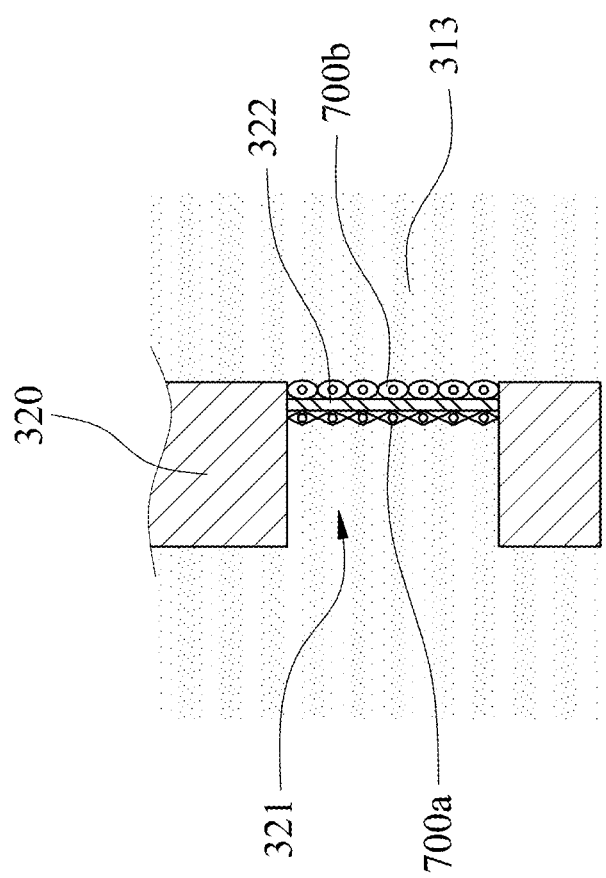
FIG. 15B is a partial enlargement schematic view showing co-culture of different cells in two-dimensional cell culture using the cell culture device according to still another embodiment of the present disclosure.
Figure 16C:
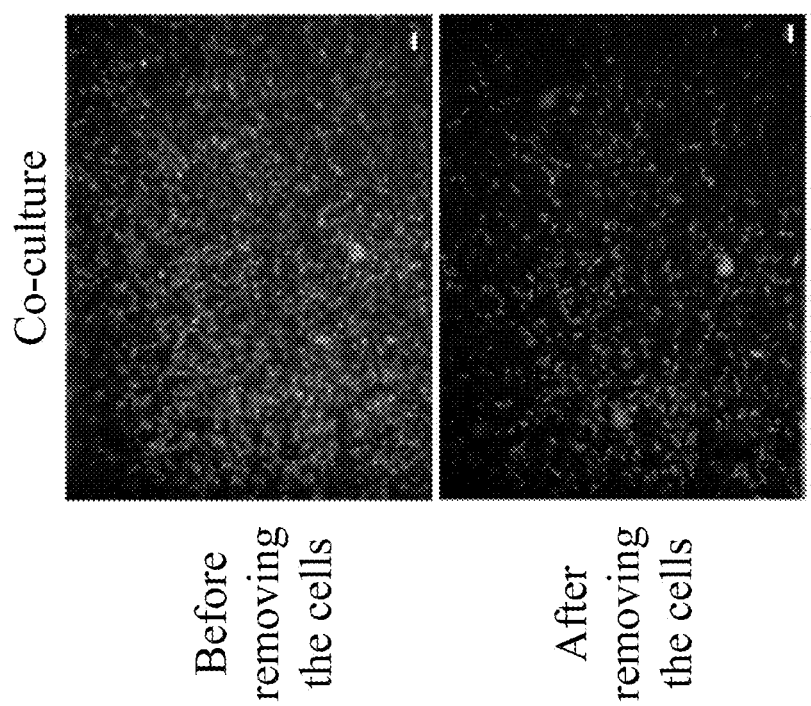

Please refer to FIG. 15B showing a partial enlargement schematic view showing co-culture of different cells in two-dimensional cell culture using the cell culture device 300 according to still another embodiment of the present disclosure. In FIG. 15B that cells 700a are attached on the culture chamber side of the first porous membrane 322 of the plug element 320, and cells 700b are attached fluid chamber side of the first porous membrane 322 of the plug element 320. In experiment 2.3, the cells 700a are A549/GFP cells, and the cells 700b are HPMECs cells, and the cell culture system 20 of FIG. 13 is used for the cell culture. Specifically, the plug element 320 is extracted from the main body 310, and HPMECs cells are seeded in the fluid chamber side of the first porous membrane 322 of the plug element 320 with 4×10⁵ cells/ml, and then A549/GFP is seeded in the culture chamber side of the first porous membrane 322 of the plug element 320 with 1.6×10⁵ cells/ml. After A549/GFP cells attached on the first porous membrane 322, the plug element 320 is plugged back into the main body 310, and the cell culture is carried out in the dynamic condition to observe the distribution of A549/GFP cells on the first porous membrane 322, thereby inferring that the condition of A549/GFP cells migrating from the culture chamber side to fluid chamber side. Please refer to FIG. 16C showing microscopy images of co-culture of A549/GFP cells and HPMECs cells in two-dimensional cell culture, and the scale bar represents 100 μm. The upper picture is the cell image of before removing the cells from the culture chamber side of the first porous membrane 322 with the cotton swab on the third day, and the lower picture is the cell image of after removing the cells from the culture chamber side of the first porous membrane 322 with the cotton swab on the third day. The migration area percentage of A549/GFP cells on the third day can be calculated by combing with the software of Image J for image analysis, and the calculation formula is shown above, and will not repeat. After calculating, the migration area percentage of co-culture of A549/GFP cells and HPMECs cells is 39.3%, and the standard deviation is 0.3% (n=3).

Figure 17:
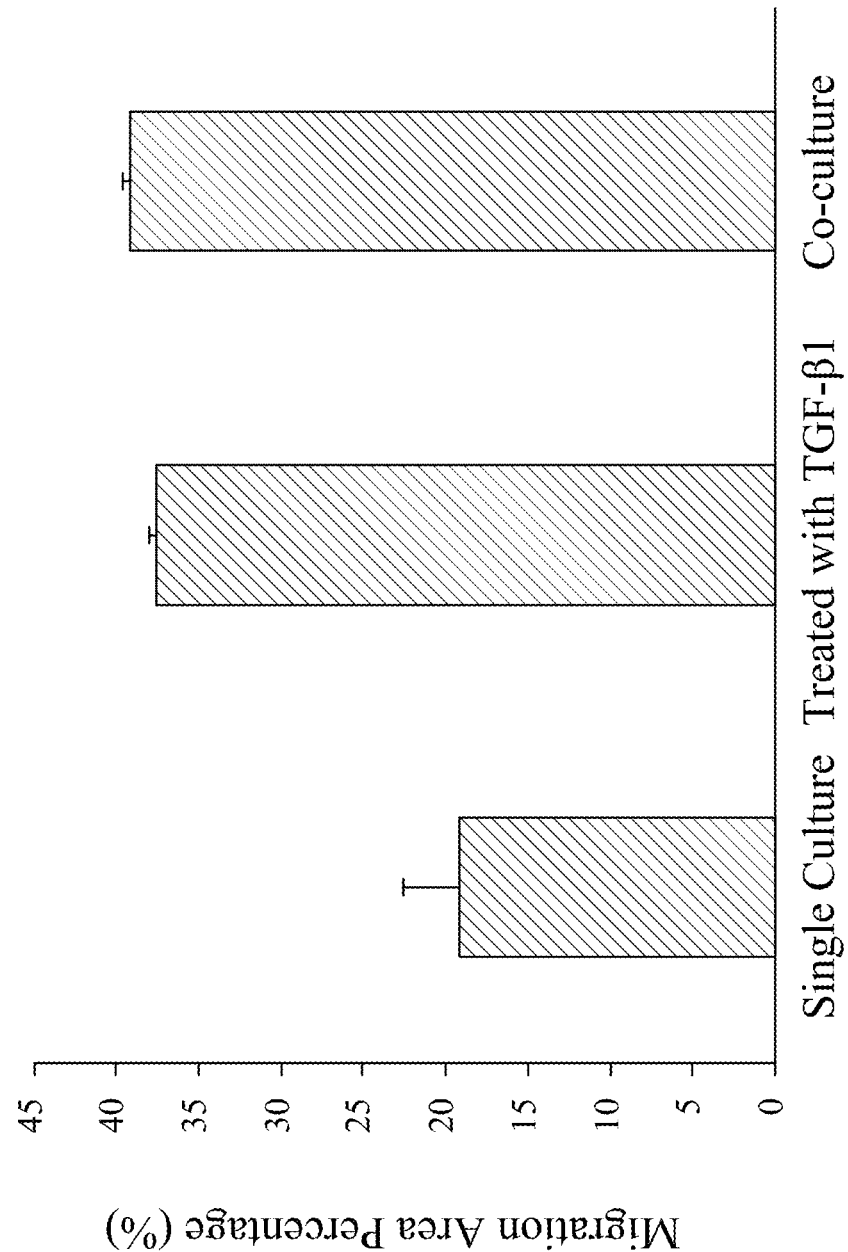
FIG. 17 is a result chart of migration area percentage of A549/GFP cells in two-dimensional cell culture.

Please refer to FIG. 17 showing a result chart of migration area percentage of A549/GFP cells in two-dimensional cell culture, and the migration area percentage from left to right are the single culture of A549/FGP cells, the single culture of A549/GFP cells treated with TGF-β1 and the co-culture of A549/GFP cells and HPMECs cell, respectively. In FIG. 17 that A549/GFP cells treated with TGF-β1 and the co-culture with HPMECs cells increase the migration area percentage compared with the single culture of A549/GFP cells, and it confirms that the cells can be cultured by the cell culture system 20 of the present experiment by controlling the fluid condition, and it is beneficial to research the application of anti-cancer drugs. Besides, the cell culture system 20 of experiment 2.3 can be used to simulate the intravasation stage of tumor metastasis, and can be used to co-culture with other stromal cells such as fibroblasts, macrophages or endothelial cells.

Three-Dimensional Cell Culture of A549/GFP Cells in the Collagen Hydrogel

Experiment 3.1

Figure 18:
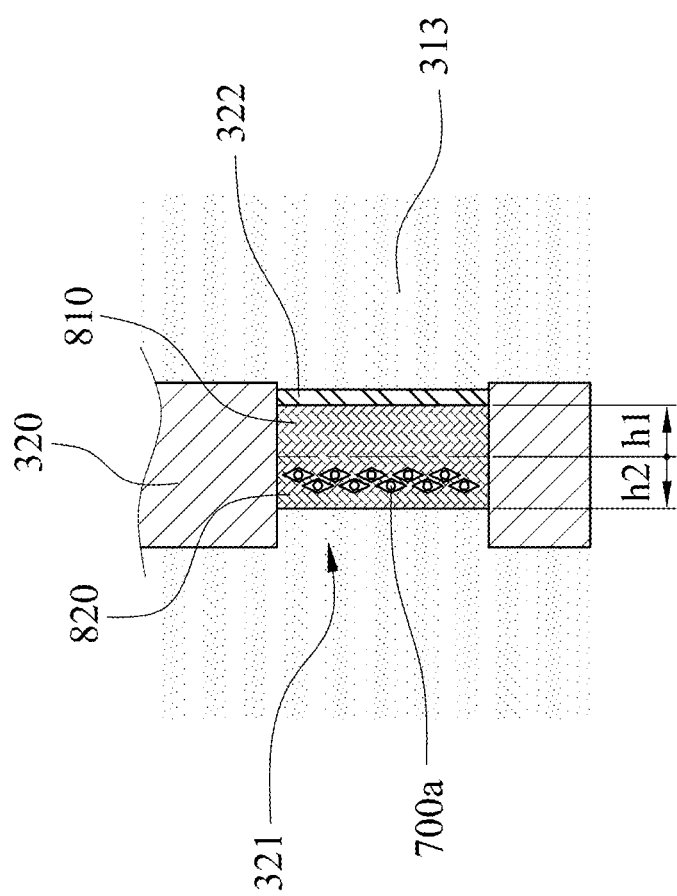
FIG. 18 is a partial enlargement schematic view of three-dimensional cell culture using the cell culture device according to still another embodiment of the present disclosure.

Please refer to FIG. 18 showing a partial enlargement schematic view of three-dimensional cell culture using the cell culture device 300 according to still another embodiment of the present disclosure. In FIG. 18, two layers of collage hydrogel are formed at the culture chamber side of the first porous membrane 322 of the plug element 320 and are a first collagen hydrogel 810 and a second collagen hydrogel 820, respectively, for observing the penetration ability of the cells in the collagen hydrogel in the cell culture device 300 of the present disclosure, thereby analyzing the migration potential of the cells. The thickness of the first collagen hydrogel 810 is h1 and no cells inside, and the thickness of the second collagen hydrogel 820 is h2 and the cells 700a inside. Thereby, the cells 700a are seeded in the collagen hydrogel before the hydrogel collagen polymerization. After polymerization, the second collagen hydrogel 820 of the cells seeded inside is obtained. In experiment 3.1, cells 700a are A549/GFP cells with 4×10⁵ cells/ml, and the thickness h1 of the first collagen hydrogel 810 is equal to the thickness h2 of the second collagen hydrogel 820 at 765 μm. The cell culture system 20 in FIG. 13 is carried out to three-dimensional cell culture for seven days at the static condition and dynamic condition, the cell migration and hyperplasia are observed for every two day, and the viewpoint of observation can be referred to FIG. 4 that the plugged element 320 is extracted and observed directly at the vertical direction of the main body 310, and then the plugged element 320 is plugged back into the main body 310 after observation. Even the experiment is carried out at the dynamic condition, and the pump 500 does not need to be interrupted. In other words, the process of the three-dimensional cell culture carried by the cell culture system 20 does not be discontinued because of observation.

Figures 19A, 19B:
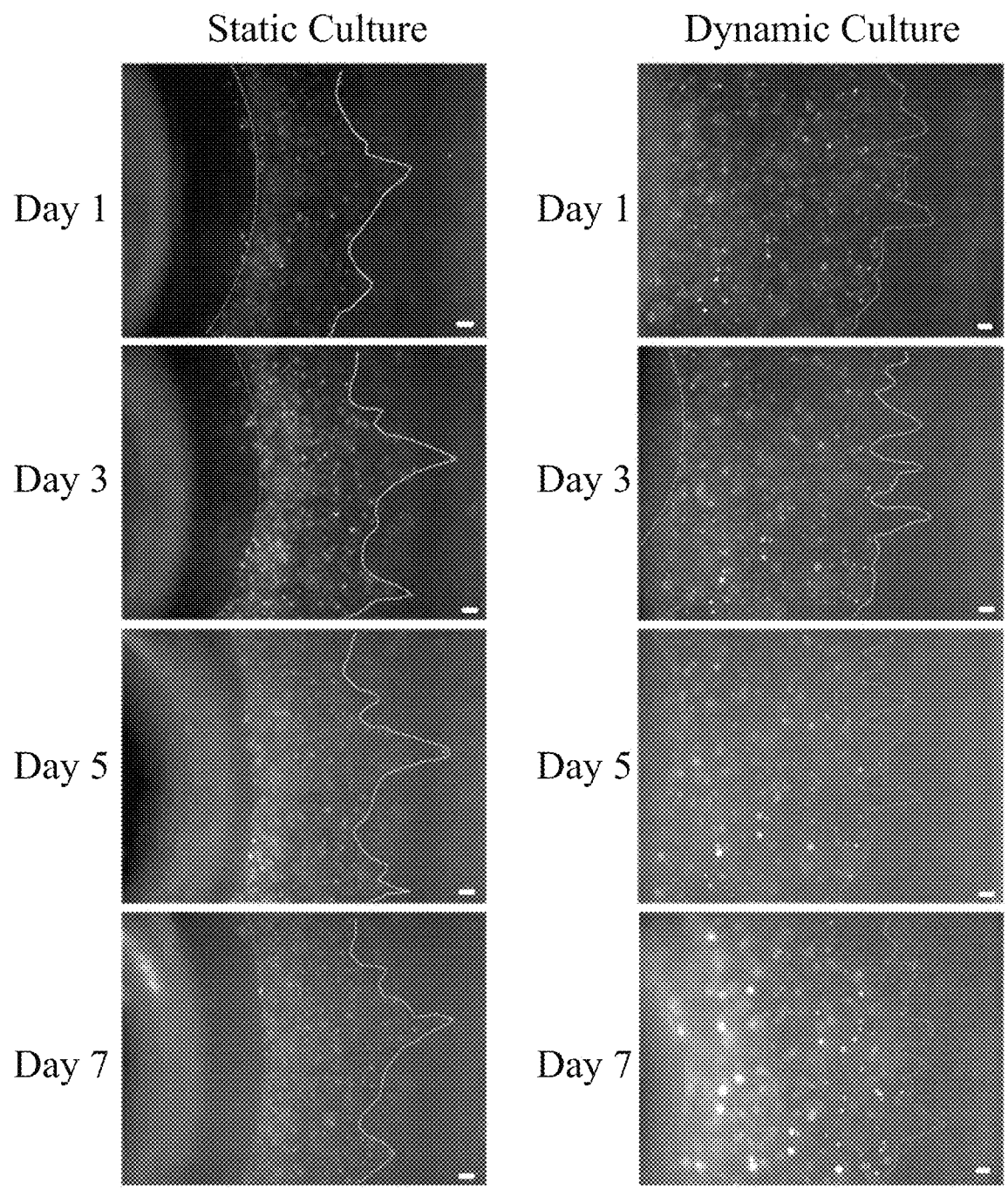
FIGS. 19A and 19B are microscopy images of A549/GFP cells in three-dimensional cell culture.

Please refer to FIGS. 19A and 19B showing microscopy images of A549/GFP cells in three-dimensional cell culture, the scale bar represents 100 μm. FIG. 19A is carried out at the static condition, FIG. 19B is carried out at the dynamic condition, the red line marks the border of the cell medium in the first collagen hydrogel 810 and the open space S3 (FIG. 9), and the green line marks the migration head of the A549/GFP cells. In FIGS. 19A and 19B, no matter at the static condition or the dynamic condition, the first migration head peak is the migration head peak of the first day, and the position of the migration head peak is maintained during the whole cell culture process that meets the result of the previous research, that is the leading cells can open up the path for the following cells during the migration of the cancer cells.

Figure 20:
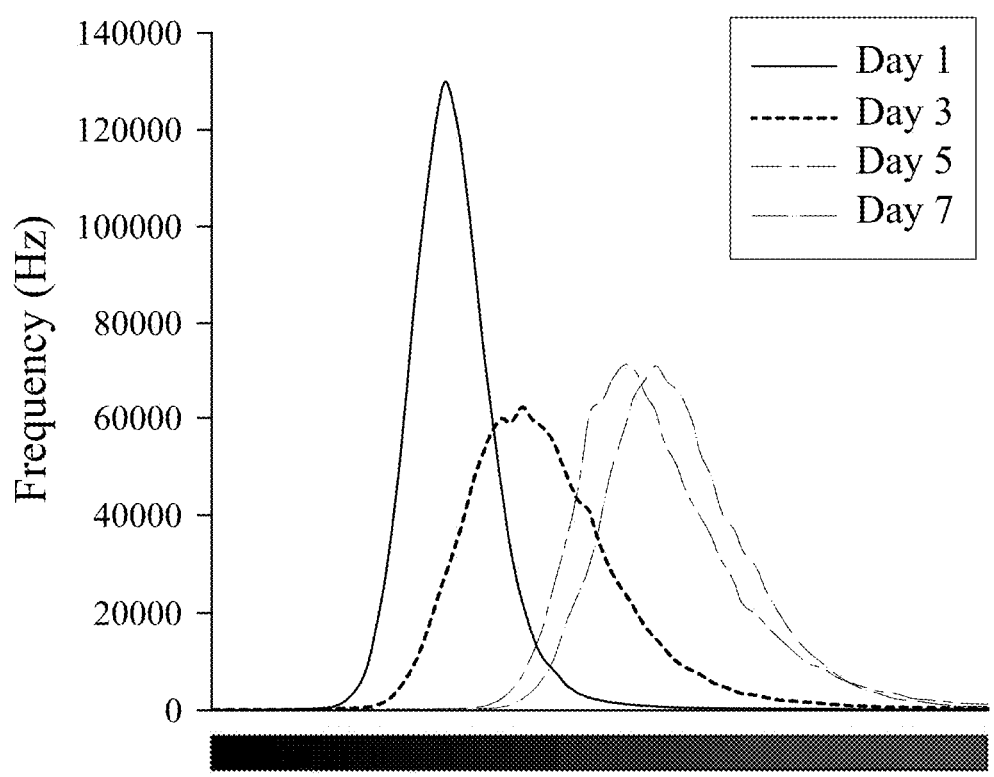
FIG. 20 is a result chart of image grayscale variation of the microscopy image of A549/GFP cells of FIGS. 19A and 19B.

Please refer to FIG. 20 showing a result chart of image grayscale variation of the microscopy image of A549/GFP cells of FIGS. 19A and 19B, wherein the more left side represents the higher image grayscale (that is the more left side image has the more black area), and the more right side represents the lower image grayscale. It can be observed from FIG. 20 that after A549/GFP cells cultured for different days, the image grayscale of the microscopy image will gradually decrease with time, and it reveals that the number or the growth area of A549/GFP cells is increased and some of the cells are proliferated at the migration head, and some of the cells are carried out migration at the migration head.

Besides, in FIGS. 19A and 19B, no matter the static condition or the dynamic condition, A549/GFP cells are not arrived at the first porous membrane 322 through the first collagen hydrogel 810 because of the too thick thickness h1 of the first collagen hydrogel 810. In addition, although the value is not shown, the thickness h1 of the first collagen hydrogel 810 decreases to 158.8 μm at another experiment, and another conditions are same, and A549/GFP cells are discovered that arrived at the first porous membrane 322 through the first collagen hydrogel 810 at the third day after seven days cell cultured. However, after that A549/GFP cells are almost maintained at the same position, and A549/GFP cells are not attached on the first porous membrane 322, it reveals that A549/GFP cells tends to maintain inside the first collagen hydrogel 810 and the second collagen hydrogel 820, and does not tend to be attached on the first porous membrane 322 or migrate to the fluid chamber 313 through the first porous membrane 322. Besides, although the value is not shown, the first collagen hydrogel 810 is omitted at another experiment that is only the second collagen hydrogel 820 and the rest of conditions are same. After seven days of cell culture, A549/GFP cells are discovered that arrive at the first porous membrane 322 at the beginning. However, after seven days, on average, only six cells are attached on the first porous membrane 322, which the number is much lower than the number of the cells of A549/GFP cells seeded in the second collagen hydrogel 820, confirming that A549/GFP cells tend to maintain in the second collagen hydrogel 820 and proliferated in the second collagen hydrogel 820.

The experiment result aforementioned is carried out the calculation of the migration area percentage and the proliferation area percentage, and the calculation formula is shown below:

Migration area percentage (%)=$(B_x/B_0) \times 100\%$, wherein $B_0$ is the area measured by the software Image J on the zeroth day, and $B_x$ is the area measured by the software Image J on the Xth day. In this moment, the area represents the area between the red line and the green line (as shown in FIGS. 19A and 19B).

Proliferation area percentage (%)=$(C_x/C_0) \times 100\%$, wherein $C_0$ is the area measured by the software Image J on the zeroth day, and $C_x$ is the area measured by the software Image J on the Xth day. In this moment, the area represents the total area of the white points delimited by the red line and the green line (as shown in the white points of FIGS. 19A and 19B). In other words, the proliferation area percentage is the variety of the detecting the fluorescence intensity.

Figure 21:
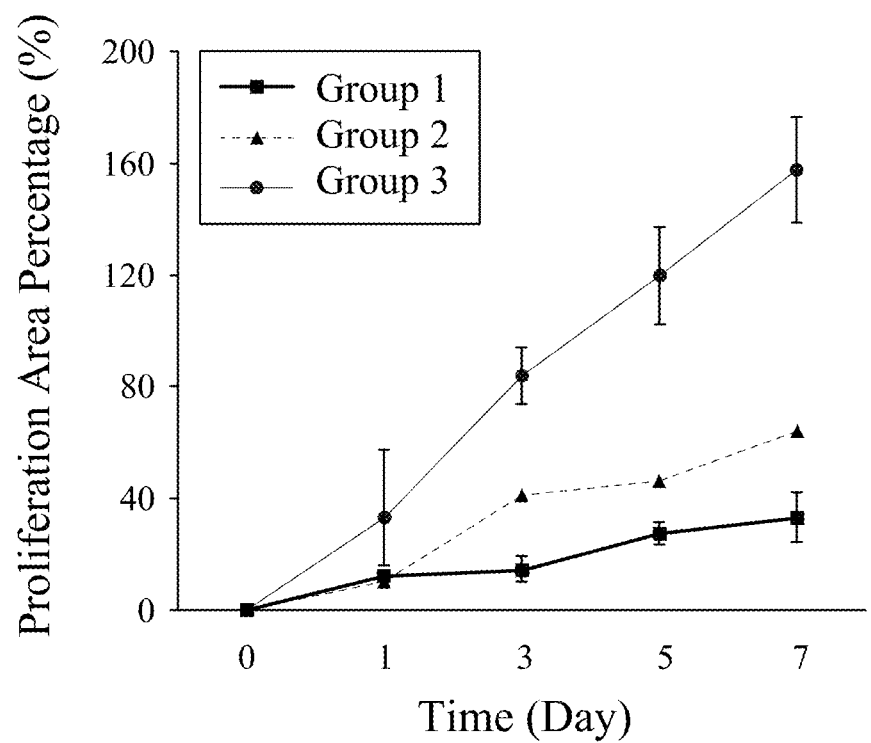
FIG. 21 is a result chart of proliferation area percentage of A549/GFP cells in three-dimensional cell culture.
Figure 22:
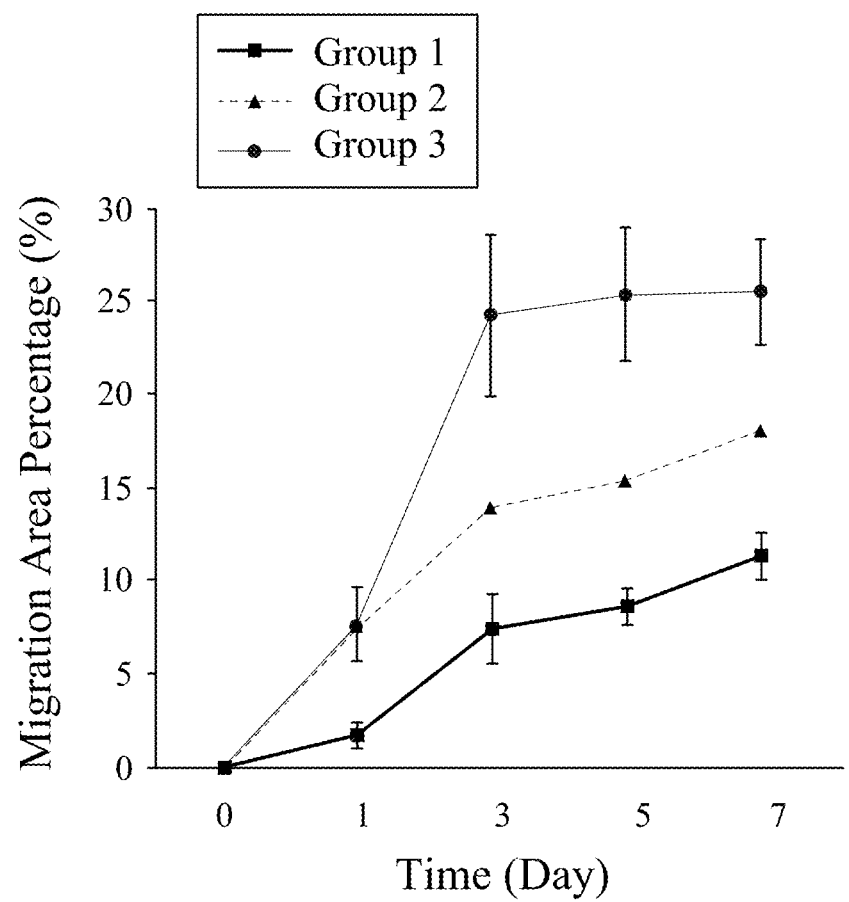
FIG. 22 is a result chart of migration area percentage of A549/GFP cells in three-dimensional cell culture.

Please refer to FIGS. 21 and 22, and FIG. 21 showing a result chart of proliferation area percentage of A549/GFP cells in three-dimensional cell culture, and FIG. 22 showing a result chart of migration area percentage of A549/GFP cells in three-dimensional cell culture. In FIGS. 21 and 22, the first group is A549/GFP cells including the first porous membrane 322 of two layers of the collagen hydrogel, which is the static culture carried out on the first porous membrane 322 shown in FIG. 18, wherein the thickness h1 of the first collagen hydrogel 810 and the thickness h2 of the second collagen hydrogel 820 are 765 μm, the second group is A549/GFP cells dynamically cultured on the first porous membrane 322 including two layers of the collagen hydrogel, wherein the thickness h1 of the first collagen hydrogel 810 and the thickness h2 of the second collagen hydrogel 820 are 765 μm, and the third group is A549/GFP cells dynamically cultured on the first porous membrane 322 including two layers of the collagen hydrogel, wherein the thickness h1 of the first collagen hydrogel 810 and the thickness h2 of the second collagen hydrogel 820 are 158.8 μm. In FIGS. 21 and 22 that it is beneficial for the proliferation and migration of cancer cells under the dynamic condition. It further confirms from the above experiment that the cell culture device and the cell culture system of the present disclosure can be successfully applied to the three-dimensional cell culture.

Collection Experiment of the A549/GFP Cells in the Fluid Chamber

Experiment 4.1

The details of performing the two-dimensional cell culture of A549/GFP cells is same as the experiment of the single culture of A549/GFP cells, the difference is only in the time of the cell culture, A549/GFP cells crossing the first porous membrane 322 and the condition of fluid circulation can be observed by extending the time of cell culture. During the experiment, the cell medium as the fluid is first replaced on the fifth day, and then replaced on every three day. The fluid container 600 is observed before replaced and the abandoned cell medium is sieved by the porous membrane at the pore size of 5 μm to collect the suspended A549/GFP cells. On the seventeenth day of cell culture, A549/GFP cells are first collected from the abandoned cell medium, A549/GFP cells are observed from the fluid container 600 on the twentieth day, cancer cells will circulate in the circulation system when the order is consistent with tumor metastasis, and then circulate in the order of the growth of the target position.

Figure 23A:
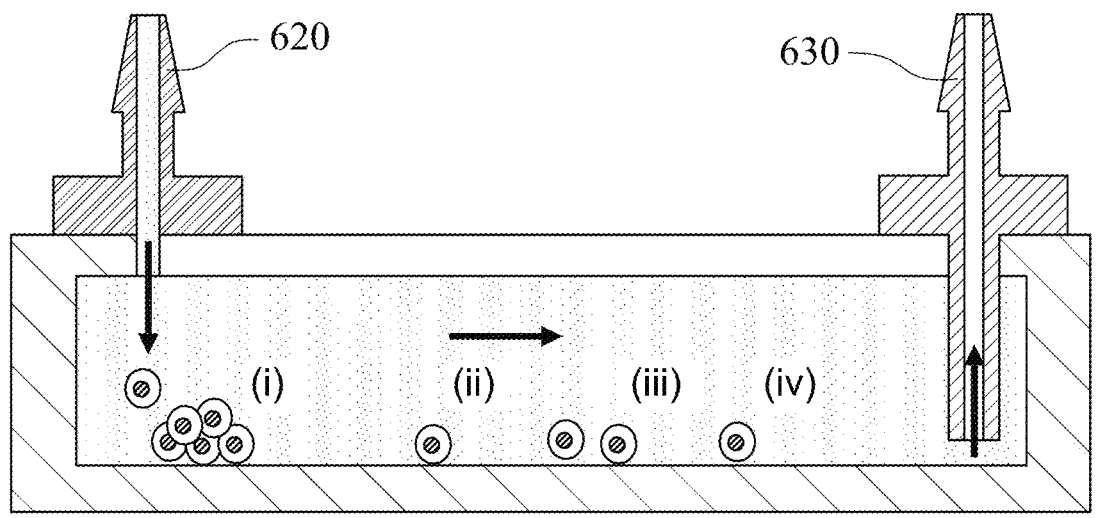
FIG. 23A is a schematic view of an observing position of A549/GFP cells in a fluid container.
Figure 23B:
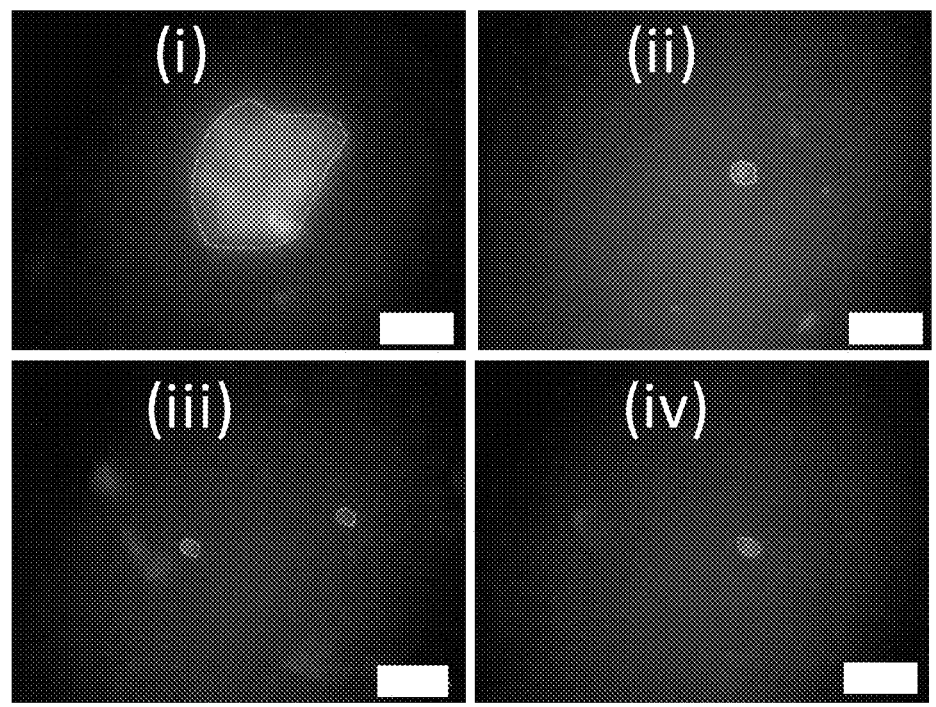
FIG. 23B is a microscopy image of A549/GFP cells in the fluid container.

Please refer to FIGS. 23A and 23B, and FIG. 23A shows a schematic view of an observing position of A549/GFP cells in a fluid container 600, and FIG. 23B is a microscopy image of A549/GFP cells in the fluid container 600. In detail, (i) to (iv) of FIG. 23B represents the microscopy image of the observation position of (i) to (iv) of FIG. 23A, respectively. In FIG. 23A, A549/GFP cells can be observed from the different position of the fluid accommodation space 610 of the fluid container 600, and it reveals that A549/GFP cells circulate with the fluid, and depart from the circulation system to growth at the target position when find the target position. Therefore, the cell culture system 20 of the present disclosure can be used to apply to the circulation stage of simulating tumor metastasis and the growth stage of the target position.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A cell culture device, comprising:
   a main body, comprising:
      a slot;
      an open groove connected with one side of the slot; and
      a fluid chamber disposed inside the main body and connected with another side of the slot; and
   a plug element, comprising:
      a first cell culture chamber;
      a first porous membrane disposed in one side of the first cell culture chamber;
      an inserting portion correspondingly plugged in the slot; and
      two extracting portions disposed at two sides of the inserting portion, respectively;
   wherein the plug element is detachably inserted in the slot, when the plug element is plugged into the slot, the first cell culture chamber is communicated with the open groove so as to form an open space, and the open space and the fluid chamber are separated by the first porous membrane;
   wherein the plug element is U-shaped, and the first cell culture chamber and the first porous membrane are disposed in the inserting portion.

2. The cell culture device of claim 1, wherein the inserting portion is made of a transparent material.

3. The cell culture device of claim 1, wherein the main body further comprises two fluid gates disposed at two sides of the fluid chamber, respectively.

4. The cell culture device of claim 1, further comprising a second cell culture chamber and a second porous membrane, the second cell culture chamber disposed inside the main body, and the second cell culture chamber and the fluid chamber are separated by the second porous membrane.

5. A cell culture system, comprising:
   a cell culture device, comprising:
      a main body, comprising a slot, an open groove, a fluid chamber and two fluid gates, wherein the open groove is connected with one side of the slot, the fluid chamber is disposed in the main body and connected with the other side of the slot, and the two fluid gates are disposed at two sides of the fluid chamber, respectively; and
      a plug element, comprising a first cell culture chamber, a first porous membrane, an inserting portion and two extracting portions, wherein the first porous membrane is disposed at one side of the first cell culture chamber, the plug element is detachably plugged into the slot, when the plug element is plugged in the slot, the first cell culture chamber is communicated with the open groove so as to form an open space, the open space and the fluid chamber are separated by the first porous membrane, the inserting portion is correspondingly plugged in the slot, the two extracting portions are disposed at two sides of the inserting portion, respectively, so that the plug element is U-shaped, and the first cell culture chamber and the first porous membrane are disposed in the inserting portion; and
   a pump connected with the two fluid gates for cyclically flowing a fluid in the fluid chamber.

6. The cell culture system of claim 5, wherein the pump is a peristaltic pump.

7. The cell culture system of claim 5, wherein the inserting portion is made of a transparent material.

8. The cell culture system of claim 5, wherein the cell culture device further comprises a second cell culture chamber and a second porous membrane, the second cell culture chamber disposed inside the main body, and the second cell culture chamber and the fluid chamber are separated by the second porous membrane.

9. The cell culture system of claim 5, further comprising:
   a fluid container, comprising:
      a fluid accommodation space; and
      two fluid exchanging ports, the two fluid exchanging ports of the fluid container connected with the fluid accommodation space;
   wherein the pump is connected with one of the fluid exchanging ports of the fluid container and one of the fluid gates of the main body, respectively, the other fluid exchanging port of the fluid container is connected with the other fluid gate of the main body, so that the fluid is cyclically flowed in the fluid chamber and the fluid accommodation space.

10. The cell culture system of claim 9, wherein the fluid container further comprises an outlet and an inlet, the outlet and the inlet is connected with the fluid accommodation space, respectively.

* * * * *